United States Patent
Heil et al.

(10) Patent No.: US 9,598,402 B2
(45) Date of Patent: Mar. 21, 2017

(54) QUINAZOLINONE ANALOGS AND USE OF QUINAZOLINONE ANALOGS FOR TREATING OR PREVENTING CERTAIN VIRAL INFECTIONS

(75) Inventors: Marintha L. Heil, Frederick, MD (US); Nicholas D. P. Cosford, La Jolla, CA (US); Robert Ardecky, La Jolla, CA (US); Jiwen Zou, La Jolla, CA (US)

(73) Assignees: Southern Research Institute, Birmingham, AL (US); Sanford-Burnham Medical Research Institute, La Jolla, CA (US)

( * ) Notice: Subject to any disclaimer, the term of this patent is extended or adjusted under 35 U.S.C. 154(b) by 375 days.

(21) Appl. No.: 14/238,346

(22) PCT Filed: Aug. 10, 2012

(86) PCT No.: PCT/US2012/050347
§ 371 (c)(1),
(2), (4) Date: May 27, 2014

(87) PCT Pub. No.: WO2013/025508
PCT Pub. Date: Feb. 21, 2013

(65) Prior Publication Data
US 2014/0256753 A1    Sep. 11, 2014

Related U.S. Application Data

(60) Provisional application No. 61/522,859, filed on Aug. 12, 2011.

(51) Int. Cl.
| | | |
|---|---|---|
| A61K 31/517 | (2006.01) | |
| C07D 413/12 | (2006.01) | |
| C07D 417/12 | (2006.01) | |
| C07D 405/12 | (2006.01) | |
| C07D 239/95 | (2006.01) | |

(52) U.S. Cl.
CPC .......... *C07D 405/12* (2013.01); *A61K 31/517* (2013.01); *C07D 239/95* (2013.01); *C07D 413/12* (2013.01); *C07D 417/12* (2013.01)

(58) Field of Classification Search
CPC ... A61K 31/517; C07D 417/12; C07D 413/12
See application file for complete search history.

(56) References Cited

U.S. PATENT DOCUMENTS

| | | |
|---|---|---|
| 6,306,899 B1 | 10/2001 | Cheng et al. |
| 2007/0066632 A1 | 3/2007 | Hart et al. |
| 2007/0191400 A1 | 8/2007 | Gregor et al. |
| 2009/0035306 A1 | 2/2009 | Pinkerton et al. |

FOREIGN PATENT DOCUMENTS

| | | |
|---|---|---|
| JP | 2007-534292 A | 11/2007 |
| WO | WO-2004/099241 A1 | 11/2004 |
| WO | WO-2010/111437 A1 | 9/2010 |
| WO | WO-2011/032277 A1 | 3/2011 |

OTHER PUBLICATIONS

Pandey et al. ("Antimicrobial studies of some novel quinazolinones fused with [1,2,4]-triazole, [1,2,4]-triazine and [1,2,4,5]-tetrazine rings". European Journal of Medicinal Chemistry vol. 44, Issue 3, Mar. 2009, pp. 1188-1197).*
Misra et al., "Synthesis and Pesticidal Activities of Some New Substituted 3H-Quinazolin-4-one Derivaties; Part XVII", Pestic. Sci., 1982, 10, 177-182.
Extended European Search Report issued Dec. 22, 2014 in EP Application No. 12824120.5.
JP Office Action in Appln No. 2014-525172 issued Apr. 26, 2016.

\* cited by examiner

*Primary Examiner* — Jeffrey S Lundgren
*Assistant Examiner* — Chris Simmons
(74) *Attorney, Agent, or Firm* — Polsinelli PC

(57) ABSTRACT

Provided is a process for treating or preventing a viral infection in a subject, wherein the viral infection is from a flavivirus selected from the group consisting of Hepatitis C Virus (genotypes 1-7) and Japanese Encephalitis Virus. The process includes administering to the subject a therapeutically effective amount of at least one compound represented by the formula: (Formula (I))

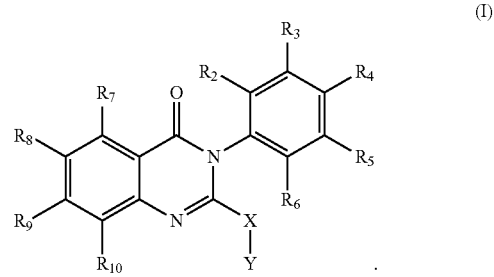

10 Claims, No Drawings

QUINAZOLINONE ANALOGS AND USE OF QUINAZOLINONE ANALOGS FOR TREATING OR PREVENTING CERTAIN VIRAL INFECTIONS

CROSS REFERENCE TO RELATED APPLICATIONS

This application is a National Phase filing under 35 U.S.C. §371 of PCT/US2012/050347 filed on Aug. 10, 2012; and this application claims priority to U.S. Provisional Application No. 61/522,859 filed on Aug. 12, 2012; the entire contents of all are hereby incorporated by reference.

FEDERALLY SPONSORED RESEARCH AND DEVELOPMENT

This invention was partially supported by grants No. 1 R03 MN084847-01 and 5U54HG0053034 from the National Institutes of Health and the US Government has certain rights in the invention.

TECHNICAL FIELD

The present disclosure relates to treating or preventing viral infection from certain flaviviruses and alphaviruses by administering a therapeutically effective amount of a quinazolinone analog, pharmaceutically acceptable salt thereof or solvate thereof. The flaviviruses treated according to this disclosure include Hepatitis C Virus (genotypes 1-7) and Japanese Encephalitis Virus. Certain of the quinazolinone compounds of the present disclosure can also be used to treat West Nile Virus. The present disclosure is also related to certain novel quinazolinone compounds. The subjects treated include humans and animals.

BACKGROUND OF DISCLOSURE

Flaviviruses and alphaviruses are positive sense RNA viruses and are important human and/or animal pathogens that can cause acute virus infections with severe diseases and/or death. Flaviviruses include members of families Flaviviridae including Dengue Virus (DENV), Murray Valley Encephalitis Virus (MVEV), Saint Louis Encephalitis Virus (SLEV), West Nile virus (WNV), Japanese Encephalitides Virus (JEV), Yellow Fever Virus (YFV) and Tick-Borne Encephalitis Virus (TBEV) and Hepciviridae including Hepatitis C Virus (HCV) and Pestiviruses including Bovine Diarrhea virus (BVDV). Alphaviruses include Venezuela Equine Encephalitides Virus (VEEV), Eastern Equine Encephalitis Virus (EEEV), Western Equine Encephalitides virus (WEEV) and Ross River Virus (RRV). For most arbovirus listed above, there is no effective vaccine or therapeutics currently available. There are no alphavirus vaccines currently available. The need to develop antiviral drugs is urgent for developing control measures and treating these diseases.

Vast amounts of research have accrued over the years related to developing treatments against viral diseases to inhibit and kill viral infections. Some of this research has resulted in agents approved for clinical use. Nevertheless, efforts continue at an ever-increasing rate in view of the extreme difficulty in uncovering promising antiviral agents.

SUMMARY OF DISCLOSURE

The present disclosure relates to treating or preventing viral infection from certain flaviviruses and alphaviruses by administering a therapeutically effective amount of a quinazolinone analog, pharmaceutically acceptable salt thereof or solvate thereof. The flaviviruses treated according to this disclosure include Hepatitis C Virus (genotypes 1-7) and Japanese Encephalitis Virus. The subjects treated include humans and animals.

According to the present disclosure a therapeutically effective amount of at least one compound represented by the formula:

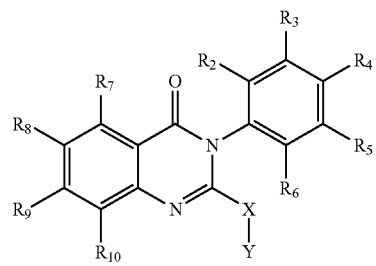

wherein X is O, S or $NR_{20}$ wherein $R_{20}$ is H or $C_{1-6}$alkyl;

Y is $(CR_{11}CR_{12})_n(CO)_pNR_{13}W$;

$R_{11}$ and $R_{12}$ are independently selected from the group consisting of H, halogen, hydroxyl, $C_{1-6}$alkoxy, amino, nitro, cyano, $CF_3$ and $C_{1-4}$alkyl;

$R_{13}$ is H or $C_{1-6}$alkyl;

n is zero, one, two, three or four, five or six;

p is zero or one;

W is hydrogen, $C_{1-6}$alkoxy, halo $C_{1-6}$alkoxy, $C_{1-6}$alkyl, halo $C_{1-6}$alkyl, hydroxy$C_{1-6}$alkyl, amino $C_{1-6}$alkyl, carboxy$C_{1-6}$alkyl, $C_{3-7}$cycloalkyl, halo $C_{3-7}$cycloalkyl; or a substituted or unsubstituted phenyl ring, a substituted or unsubstituted five- or 6-membered saturated or unsaturated heterocyclic ring containing one, two, three or four heteroatoms independently chosen from O, N and S, or a nine- or ten- or eleven-membered fused bicyclic ring containing a phenyl ring or a six-membered heteroaromatic ring as just defined, fused to either a saturated or unsaturated five- or six- or seven-membered ring, which can be substituted or unsubstituted, when substituted any of the above rings can be substituted by halogen, $C_{1-6}$alkyl, $C_{2-6}$alkenyl, $C_{2-6}$alkynyl, nitro, cyano, $C_{3-7}$cycloalkyl, hydroxy, $C_{1-6}$alkoxy, halo$C_{1-6}$alkyl, halo $C_{1-6}$alkoxy, hydroxy $C_{1-6}$alkyl, hydroxy $C_{1-6}$alkoxy, phenyl, an unsubstituted five-membered heteroaromatic ring as just described, a six-membered heteroaromatic ring as just described, a six-membered saturated ring as just described or $NR_{14}R_{15}$; each $R_{14}$ and $R_{15}$ is independently hydrogen or $C_{1-6}$alkyl or $R_{14}$ and $R_{15}$, together with the nitrogen atom to which they are attached, may form a saturated 4-7 membered ring;

and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, formyl, $CF_3$, $S(C_{1-4}$alkyl), $S(O)C_{1-4}$ alkyl, $S(O)_2C_{1-4}$alkyl, $C_{1-4}$alkylcarbonyl, $C_{1-6}$alkyl, hydroxy $C_{1-6}$alkyl, $C_{1-6}$alkoxy, halo$C_{1-6}$alkoxy, hydroxy $C_{1-6}$ alkoxy, $C_{2-6}$alkenyl, $C_{2-6}$alkynyl, $C_{1-6}$alkylamino, di($C_{1-6}$alkyl)amino; pharmaceutically acceptable salts thereof; solvates thereof and deuterated forms thereof; is administered to a subject in need thereof.

The present disclosure also relates to compounds represented by the formula:

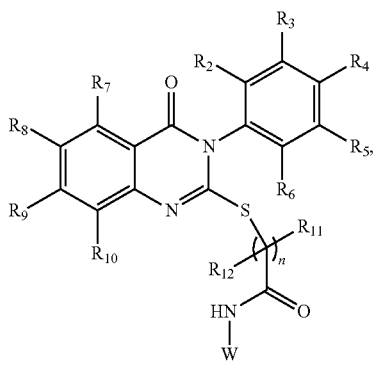

wherein W is a substituted or unsubstituted thiazoyl group and when substituted W is substituted with a $C_{1-6}$alkyl, phenyl or benzoyl group, and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, $CF_3$, and $C_{1-6}$alkyl; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof.

A further aspect of the present disclosure is concerned with a process for treating or preventing a viral infection in a subject from Hepatitis C Virus, by administering to the subject a therapeutically effective amount of at least one compound selected from the group consisting of 2-[3-(3,4-dichlorophenyl)-4-oxo(3-hydroquinazolin-2-ylthio)]-N-(4-phenyl(1,3-thiazol-2-yl))acetamide; N-benzothiazol-5-yl-2-[3-(3,4-dichlorophenyl)-4-oxo(3-hydroquinazolin-2-ylthio)]acetamide; 2-[3-(3,4-dichlorophenyl)-4-oxo(3-hydroquinazolin-2-ylthio)]-N-(4-methyl(1,3-thiazol-2-yl))acetamide; N-(2,3-dihydro-1H-inden-5-yl)-2-(4-oxo-3-phenyl-3,4-dihydroquinazolin-2-yl)thio) acetamide; 2-[3-(3-chloro-4-fluorophenyl)-4-oxo(3-hydroquinazolin-2-ylthio)]-N-indan-5-ylacetamide; 2-[3-(3,4-dichlorophenyl)-4-oxo(3-hydroquinazolin-2-ylthio)]-N-indan-5-ylacetamide; 2-(5-fluoro-4-oxo-3-phenyl(3-hydroquinazolin-2-ylthio))-N-indan-5-ylacetamide; N-indan-5-yl-2-(8-methyl-4-oxo-3-phenyl(3-hydroquinazolin-2-ylthio))acetamide; N-indan-5-yl-2-(8-methoxy-4-oxo-3-phenyl(3-hydroquinazolin-2-ylthio))acetamide; 2-[3-(3,4-dichlorophenyl)-4-oxo(3-hydroquinazolin-2-ylthio)]-N-indan-4-ylacetamide; N-(2H-benzo[d]1,3-dioxolen-5-yl)-2-[3-(3,4-dichlorophenyl)-4-oxo(3-hydroquinazolin-2-ylthio)]acetamide; 3-[3-(3-chloro-4-fluorophenyl)-4-oxo(3-hydroquinazolin-2-ylthio)]-N-indan-5-ylpropanamide; 2-[3-(3-chloro-4-fluorophenyl)-4-oxo(3-hydroquinazolin-2-ylthio)]-N-indan-4-ylacetamide; N-(2H-benzo[3,4-d]1,3-dioxolan-5-yl)-2-[3-(3-chloro-4-fluorophenyl)-4-oxo(3-hydroquinazolin-2-ylthio)]acetamide; 2-[3-(3,4-difluorophenyl)-4-oxo(3-hydroquinazolin-2-ylthio)]-N-indan-4-ylacetamide; 2-[3-(3,4-difluorophenyl)-4-oxo(3-hydroquinazolin-2-ylthio)]-N-indan-5-ylacetamide; 2-(5-fluoro-4-oxo-3-phenyl(3-hydroquinazolin-2-ylthio))-N-(1,2,3,4-tetrahydronaphthyl)acetamide; 2-[3-(4-chloro-3-fluorophenyl)-5-fluoro-4-oxo(3-hydroquinazolin-2-ylthio)]-N-indan-5-ylacetamide; 2-[5-fluoro-4-oxo-3-(3,4,5-trifluorophenyl)(3-hydroquinazolin-2-ylthio)]-N-indan-5-ylacetamide; and 2-[3-(3,4-dichlorophenyl)-5-fluoro-4-oxo (3-hydroquinazolin-2-ylthio)]-N-indan-5-ylacetamide; pharmaceutically acceptable salts thereof; solvates thereof and deuterated forms thereof.

A still further aspect of the present disclosure relates to a process for treating or preventing a viral infection in a subject from Japanese Encephalitis Virus by administering to the subject a therapeutically effective amount of at least one compound selected from the group consisting of 2-(5-fluoro-4-oxo-3-phenyl(3-hydroquinazolin-2-ylthio))-N-indan-5-ylacetamide; 2-[3-(3,4-dichlorophenyl)-4-oxo(3-hydroquinazolin-2-ylthio)]-N-indan-4-ylacetamide; 2-[3-(2,6-dichlorophenyl)-4-oxo(3-hydroquinazolin-2-ylthio)]-N-indan-5-ylacetamide; and 2-(8-fluoro-4-oxo-3-phenyl(3-hydroquinazolin-2-ylthio))-N-indan-5-ylacetamide; pharmaceutically acceptable salts thereof; solvates thereof and deuterated forms thereof.

Another aspect of the present disclosure is concerned with treating or preventing a viral infection in a subject from West Nile Virus by administering to the subject a therapeutically effective amount of at least one compound selected from the group consisting of: 2-[3-(2-fluorophenyl)-4-oxo(3-hydroquinazolin-2-ylthio)]-N-indan-5-ylacetamide; 2-[3-(3-chloro-4-fluorophenyl)-4-oxo(3-hydroquinazolin-2-ylthio)]-N-indan-5-ylacetamide; 2-[3-(3,4-dichlorophenyl)-4-oxo(3-hydroquinazolin-2-ylthio)]-N-indan-5-ylacetamide; 2-[3-(3,5-dichlorophenyl)-4-oxo(3-hydroquinazolin-2-ylthio)]-N-indan-5-ylacetamide; 2-[3-(3,4-difluorophenyl)-4-oxo(3-hydroquinazolin-2-ylthio)]-N-indan-5-ylacetamide, 2-[3-(3,4-dichlorophenyl)-5-fluoro-4-oxo(3-hydroquinazolin-2-ylthio)]-N-indan-5-ylacetamide; N-indan-5-yl-2-(4-oxo-3-phenyl(3-hydroquinazolin-2-ylthio))acetamide; 2-[3-(4-chloro-3-methylphenyl)-4-oxo(3-hydroquinazolin-2-ylthio)]-N-indan-5-ylacetamide; 2-[3-(4-fluoro-3-methylphenyl)-4-oxo(3-hydroquinazolin-2-ylthio)]-N-indan-5-ylacetamide; N-indan-5-yl-2-[4-oxo-3-(3,4,5-trifluorophenyl)(3-hydroquinazolin-2-ylthio)]acetamide; 2-[3-(3-bromo-4-methylphenyl)-4-oxo(3-hydroquinazolin-2-ylthio)]-N-indan-5-ylacetamide; 2-[3-(3,4-dichlorophenyl)-8-fluoro-4-oxo(3-hydroquinazolin-2-ylthio)]-N-indan-5-ylacetamide; 2-[3-(3,5-difluorophenyl)-4-oxo(3-hydroquinazolin-2-ylthio)]-N-indan-5-ylacetamide; 2-[3-(3,5-dichlorophenyl)-8-fluoro-4-oxo(3-hydroquinazolin-2-ylthio)]-N-indan-5-ylacetamide; 2-[3-(2,6-dichlorophenyl)-4-oxo(3-hydroquinazolin-2-ylthio)]-N-indan-5-ylacetamide; 2-[3-(3-bromo-4-chlorophenyl)-4-oxo(3-hydroquinazolin-2-ylthio)]-N-indan-5-ylacetamide; 2-(8-fluoro-4-oxo-3-phenyl(3-hydroquinazolin-2-ylthio))-N-indan-5-ylacetamide; and 2-[3-(4,5-difluoro(2-pyridyl))-4-oxo(3-hydroquinazolin-2-ylthio)]-N-indan-5-ylacetamide; pharmaceutically acceptable salts thereof; solvates thereof and deuterated forms thereof.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES FOR CARRYING OUT DISCLOSURE

The present disclosure is concerned with a process for treating or preventing a viral infection in a subject, wherein the viral infection is from a flavivirus selected from the group consisting of Hepatitis C Virus (genotypes 1-7) and Japanese Encephalitis Virus. The process comprises administering to the subject a therapeutically effective amount of at least one compound represented by the formula:

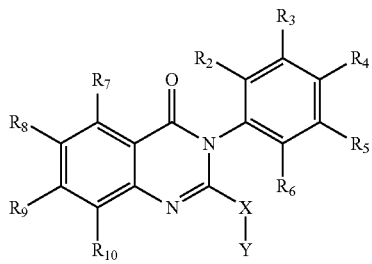

wherein X is O, S or $NR_{20}$ wherein $R_{20}$ is H or $C_{1-6}$alkyl; X is more typically S;

Y is $(CR_{11}CR_{12})_n(CO)_pNR_{13}W$;

$R_{11}$ and $R_{12}$ are independently selected from the group consisting of H, halogen, hydroxyl, $C_{1-6}$alkoxy, amino, nitro, cyano, $CF_3$ and $C_{1-4}$alkyl;

$R_{13}$ is H or $C_{1-6}$alkyl;

n is zero, one, two, three, four, five or six; and more typically one, two or three;

p is zero or one; more typically p is one

W is hydrogen, $C_{1-6}$alkoxy, halo $C_{1-6}$alkoxy, $C_{1-6}$alkyl, halo $C_{1-6}$alkyl, hydroxy$C_{1-6}$alkyl, amino $C_{1-6}$alkyl, carboxy$C_{1-6}$alkyl, $C_{3-7}$cycloalkyl, halo $C_{3-7}$cycloalkyl; or a substituted or unsubstituted phenyl ring, a substituted or unsubstituted five- or 6-membered saturated or unsaturated heterocyclic ring containing one, two, three or four heteroatoms independently chosen from O, N and S, or a nine- or ten- or eleven-membered fused bicyclic ring containing a phenyl ring or a six-membered heteroaromatic ring as just defined, fused to either a saturated or unsaturated five- or six- or seven-membered ring, which can be substituted or unsubstituted, when substituted any of the above rings can be substituted by halogen, $C_{1-6}$alkyl, $C_{2-6}$alkenyl, $C_{2-6}$alkynyl, nitro, cyano, $C_{3-7}$cycloalkyl, hydroxy, $C_{1-6}$alkoxy, halo$C_{1-6}$alkyl, halo $C_{1-6}$alkoxy, hydroxy $C_{1-6}$alkyl, hydroxy $C_{1-6}$alkoxy, phenyl, an unsubstituted five-membered heteroaromatic ring as just described, a six-membered heteroaromatic ring as just described, a six-membered saturated ring as just described or $NR_{14}R_{15}$; each $R_{14}$ and $R_{15}$ is independently hydrogen or $C_{1-6}$alkyl or $R_{14}$ and $R_{15}$, together with the nitrogen atom to which they are attached, may form a saturated 4-7 membered ring;

and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, formyl, $CF_3$, $S(C_{1-4}$ alkyl), $S(O)C_{1-4}$ alkyl, $S(O)_2C_{1-4}$alkyl, $C_{1-4}$alkylcarbonyl, $C_{1-6}$alkyl, hydroxy $C_{1-6}$alkyl, $C_{1-6}$alkoxy, halo$C_{1-6}$alkoxy, hydroxy $C_{1-6}$ alkoxy, $C_{2-6}$alkenyl, $C_{2-6}$alkynyl, $C_{1-6}$alkylamino, di($C_{1-6}$alkyl)amino; pharmaceutically acceptable salts thereof; solvates thereof and deuterated forms thereof.

According to more typical aspects of the present disclosure, Y in the above formula is $X(C_2H_2)C(=O)NH$ and W is a member selected from the group consisting of

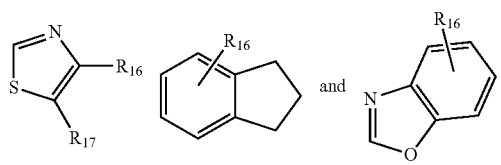

wherein $R_{16}$ and $R_{17}$ each is independently selected from the group consisting of H, halo, alkyl, alkoxy and aryl or $R_{16}$ and $R_{17}$ can be attached to form a five, six or seven membered ring, that can be substituted or unsubstituted and wherein the ring can be a hetero ring containing one or more of O, S and N hetero atoms in the ring. Examples of some even more typical W members are represented by the following formulae:

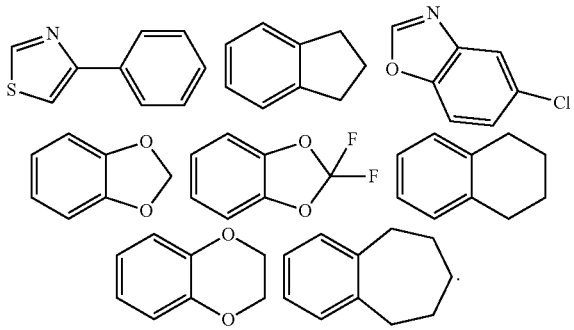

Some even more typical compounds employed according to the present invention can be represented by the following formula:

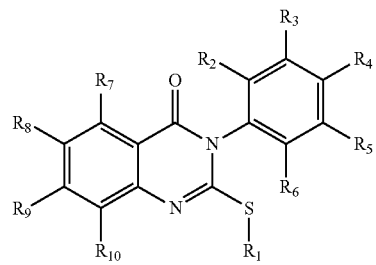

wherein $R_1$ is represented by the formula:

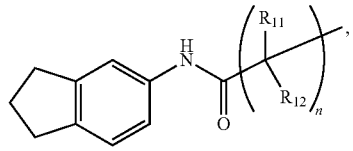

and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, formyl, $CF_3$, $S(C_{1-4}$ alkyl), $S(O)C_{1-4}$ alkyl, $S(O)_2C_{1-4}$alkyl, $C_{1-4}$alkylcarbonyl, $C_{1-6}$alkyl, hydroxy $C_{1-6}$alkyl, $C_{1-6}$alkoxy, halo$C_{1-6}$alkoxy, hydroxy $C_{1-6}$ alkoxy, $C_{2-6}$alkenyl, $C_{2-6}$alkynyl, $C_{1-6}$alkylamino, di($C_{1-6}$alkyl)amino; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof.

The present disclosure is also directed to compounds represented by the formula:

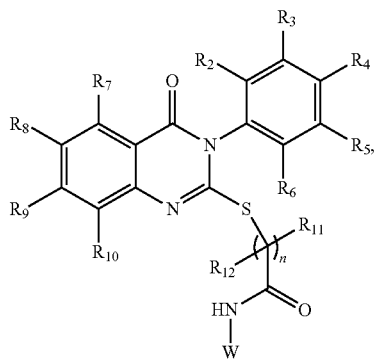

wherein W is a substituted or unsubstituted thiazoyl group and when substituted W is substituted with a $C_{1-6}$alkyl, phenyl or benzoyl group, and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, $CF_3$, and $C_{1-6}$alkyl; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof. Some examples of compounds according to this formula are 2-[3-(3,4-dichlorophenyl)-4-oxo(3-hydroquinazolin-2-ylthio)]-N-(4-phenyl(1,3-thiazol-2-yl))acetamide; N-benzothiazol-5-yl-2-[3-(3,4-dichlorophenyl)-4-oxo(3-hydroquinazolin-2-ylthio)]acetamide; and 2-[3-(3,4-dichlorophenyl)-4-oxo(3-hydroquinazolin-2-ylthio)]-N-(4-methyl(1,3-thiazol-2-yl))acetamide; pharmaceutically acceptable salts thereof; solvates thereof and deuterated forms thereof.

The present disclosure is also concerned with a process for treating or preventing a viral infection in a subject from West Nile Virus by administering to the subject a therapeutically effective amount of at least one compound selected from the group consisting of: 2-[3-(2-fluorophenyl)-4-oxo(3-hydroquinazolin-2-ylthio)]-N-indan-5-ylacetamide; 2-[3-(3-chloro-4-fluorophenyl)-4-oxo(3-hydroquinazolin-2-ylthio)]-N-indan-5-ylacetamide; 2-[3-(3,4-dichlorophenyl)-4-oxo(3-hydroquinazolin-2-ylthio)]-N-indan-5-ylacetamide; 2-[3-(3,5-dichlorophenyl)-4-oxo(3-hydroquinazolin-2-ylthio)]-N-indan-5-ylacetamide; 2-[3-(3,4-difluorophenyl)-4-oxo(3-hydroquinazolin-2-ylthio)]-N-indan-5-ylacetamide, 2-[3-(3,4-dichlorophenyl)-5-fluoro-4-oxo(3-hydroquinazolin-2-ylthio)]-N-indan-5-ylacetamide; N-indan-5-yl-2-(4-oxo-3-phenyl(3-hydroquinazolin-2-ylthio))acetamide; 2-[3-(4-chloro-3-methylphenyl)-4-oxo(3-hydroquinazolin-2-ylthio)]-N-indan-5-ylacetamide; 2-[3-(4-fluoro-3-methylphenyl)-4-oxo(3-hydroquinazolin-2-ylthio)]-N-indan-5-ylacetamide; N-indan-5-yl-2-[4-oxo-3-(3,4,5-trifluorophenyl)(3-hydroquinazolin-2-ylthio)]acetamide; 2-[3-(3-bromo-4-methylphenyl)-4-oxo(3-hydroquinazolin-2-ylthio)]-N-indan-5-ylacetamide; 2-[3-(3,4-dichlorophenyl)-8-fluoro-4-oxo(3-hydroquinazolin-2-ylthio)]-N-indan-5-ylacetamide; 2-[3-(3,5-difluorophenyl)-4-oxo(3-hydroquinazolin-2-ylthio)]-N-indan-5-ylacetamide; 2-[3-(3,5-dichlorophenyl)-8-fluoro-4-oxo(3-hydroquinazolin-2-ylthio)]-N-indan-5-ylacetamide; 2-[3-(2,6-dichlorophenyl)-4-oxo(3-hydroquinazolin-2-ylthio)]-N-indan-5-ylacetamide; 2-[3-(3-bromo-4-chlorophenyl)-4-oxo(3-hydroquinazolin-2-ylthio)]-N-indan-5-ylacetamide; 2-(8-fluoro-4-oxo-3-phenyl(3-hydroquinazolin-2-ylthio))-N-indan-5-ylacetamide; and 2-[3-(4,5-difluoro(2-pyridyl))-4-oxo(3-hydroquinazolin-2-ylthio)]-N-indan-5-ylacetamide; pharmaceutically acceptable salts thereof; solvates thereof and deuterated forms thereof.

The term "alkyl" refers to straight or branched chain unsubstituted hydrocarbon groups of typically 1 to 22 carbon atoms, more typically 1 to 8 carbon atoms, and even more typically 1 to 4 carbon atoms.

Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

Examples of halo groups are Cl, F, Br and I.

The term "aryl" refers to monocyclic or bicyclic aromatic hydrocarbon groups having 6 to 12 carbon atoms in the ring portion, such as phenyl, naphthyl, biphenyl, and diphenyl groups.

The term "cycloalkyl" refers to cyclic hydrocarbon ring systems typically containing 3-6 carbon atoms, with typical examples being cyclopropyl, cyclobutyl, cyclopentyl, and cyclohexyl.

Suitable alkenyl groups typically contain 2-6 carbon atoms and include ethenyl and propenyl.

Suitable alkynyl groups typically contain 1-6 carbon atoms and include ethynyl and propynyl.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, isopyrrole, 1,2,3-triazole, 1,2,4-triazole, oxazole, thiazole, pyrimidine, aziridines, thiazole, 1,2,3-oxadiazole, thiazine, pyrrolidine, oxaziranes, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkyl-pyrimidines, N5-benzylpyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

It is understood that the compounds of the present disclosure relate to all optical isomers and stereo-isomers at the various possible atoms of the molecule, unless specified otherwise. Compounds may be separated or prepare as their pure enantiomers or diasteriomers by crystallization, chromatography or synthesis.

The deuterated forms contain heavy hydrogen including deuterium. The carbon labeled forms may contain carbon 13.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphtalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Solvates" refers to the compound formed by the interaction of a solvent and a solute and includes hydrates. Solvates are usually crystalline solid adducts containing solvent molecules within the crystal structure, in either stoichiometric or non-stoichiometric proportions.

The terms "effective amount" or "therapeutically effective amount" refer to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the disclosure, the term preferably encompasses a non-toxic amount that improves overall therapy, reduces or avoids symptoms or causes of disease, or enhances the therapeutic efficacy of or synergies with another therapeutic agent.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

More typical compounds employed according to the present invention can be synthesized according to the Scheme 1:

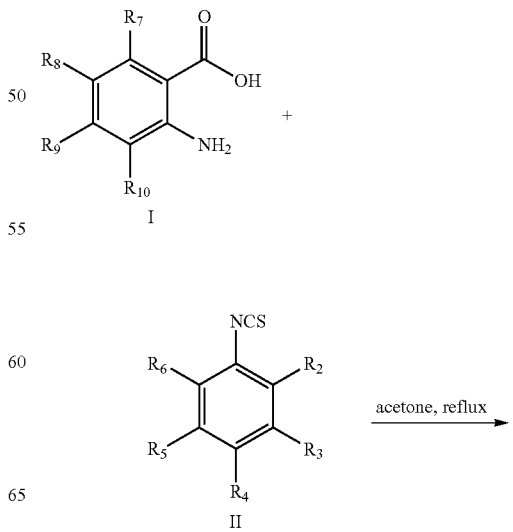

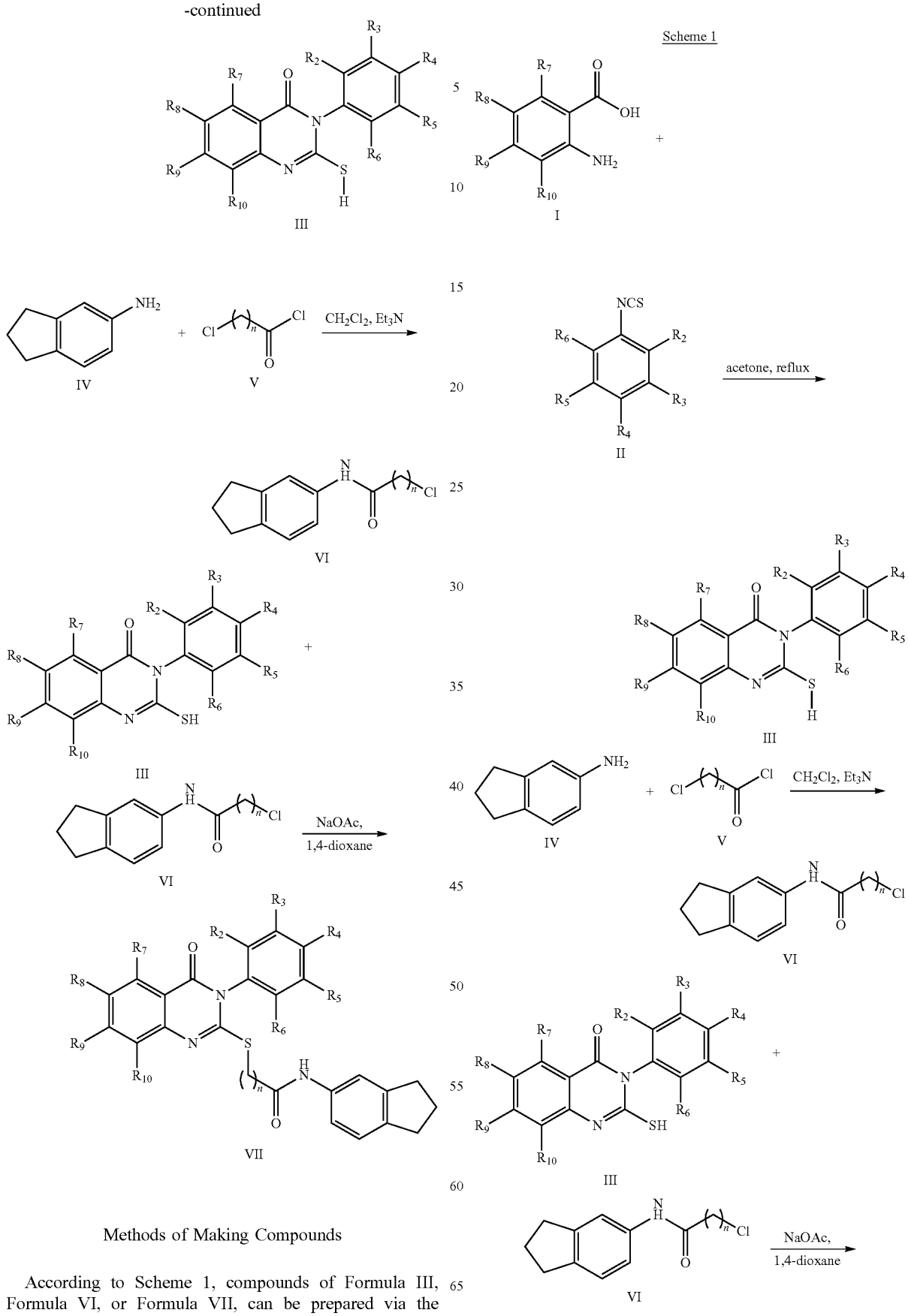
Methods of Making Compounds
According to Scheme 1, compounds of Formula III, Formula VI, or Formula VII, can be prepared via the following reaction scheme:

-continued

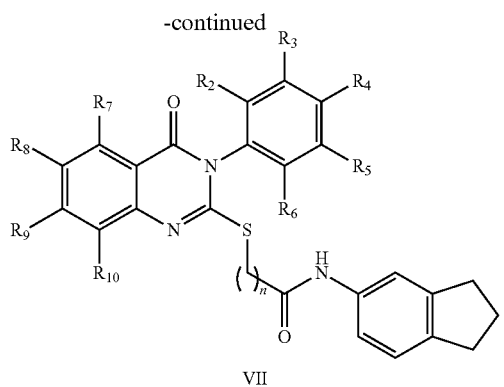

VII

Reaction of an anthranilic acid I with a thioisocyanate II in refluxing acetone or similar inert organic solvents, gives rise to compounds of Formula III. Treatment of 2,3-dihydro-1H-inden-5-amine IV or any aromatic amine with chloroacetyl chloride or similar acid chloride V in dichloromethane or similar organic solvent, containing an amine base such as triethyl amine gives rise to compounds of Formula VI. When Compound III and Compound VI are treated with sodium acetate or similar base, in 1,4-doxane or a comparable organic solvent, compounds of type VIII are formed. This reaction is preferably carried out at a temperature between 0° C. and 50° C.

EXAMPLES

Preparation of 2-mercapto-3-phenylquinazolin-4(3H)-ones

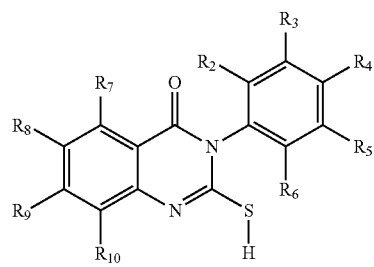

General Procedure A

Example A1

2-mercapto-3-phenylquinazolin-4(3H)-one

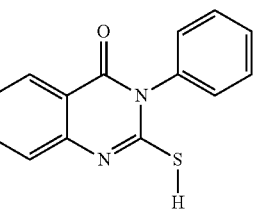

2-Amino benzoic acid (1 g, 7.29 mmol) and phenylthioisocyante (1.18 g, 8.75 mmol) were dissolved in 20 mL of acetone and the reaction mixture was refluxed and checked by TLC. When the reaction was determined to be complete by TLC, the reaction mixture was cooled to room temperature and filtered. The residue was crystallized from ethanol to afford a white solid 465 mg (25% yield) of the target compound 2-Mercapto-3-phenylquinazolin-4(3H)-one. 1H NMR (400 MHz, DMSO-d6) δ 7.19 (m, 1H), 7.38-7.45 (m, 4H), 7.55-7.64 (m, 3H), 8.03 (m, 1H), MS (EI) 255 [(M+1)+]*.

Example A2

3-(3,4-dichlorophenyl)-2-mercaptoquinazolin-4(3H)-one

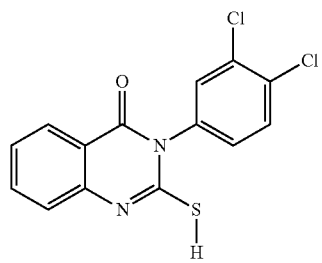

The title compound was prepared from the reaction of 2-amino benzoic acid with 3,4-dichlorophenylthioisocyante according to the general procedure A. Obtained as a white solid MS (EI) 324 [(M+1)+].

Example A3

3-(3-chloro-4-fluorophenyl)-2-mercaptoquinazolin-4(3H)-one

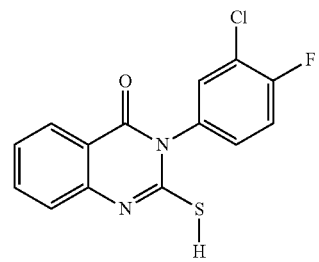

The title compound was prepared from the reaction of 2-amino benzoic acid with 3-chloro-4-fluorophenylthioisocyante according to the general procedure A. Obtained as a white solid MS (EI) 307 [(M+1)+].

Example A4

3-(3,4,5-trifluorophenyl)-2-mercaptoquinazolin-4(3H)-one

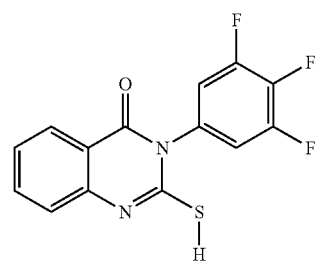 [SMILES: O=c1c2ccccc2nc(S)n1-c1cc(F)c(F)c(F)c1]

The title compound was prepared from the reaction of 2-amino benzoic acid with 3,4,5-trifluorofluorophenylthioisocyante according to the general procedure A. Obtained as a white solid MS (EI) 309 [(M+1)+].

Example A5

3-(3,4-difluorophenyl)-2-mercaptoquinazolin-4(3H)-one

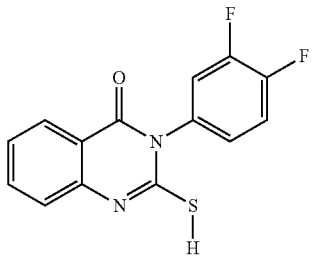 [SMILES: O=c1c2ccccc2nc(S)n1-c1ccc(F)c(F)c1]

The title compound was prepared from the reaction of 2-amino benzoic acid with 3,4-difluorofluorophenylthioisocyante according to the general procedure A. Obtained as a white solid MS (EI) 291 [(M+1)+].

Example A6

3-(3-fluoro-4-chlorophenyl)-2-mercaptoquinazolin-4(3H)-one

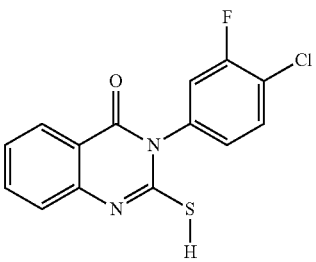 [SMILES: O=c1c2ccccc2nc(S)n1-c1ccc(Cl)c(F)c1]

The title compound was prepared from the reaction of 2-amino benzoic acid with 3-fluoro-4-chlorofluorophenylthioisocyante according to the general procedure A. Obtained as a white solid MS (EI) 307 [(M+1)+].

Example A7

5-fluoro-2-mercapto-3-phenylquinazolin-4(3H)-one

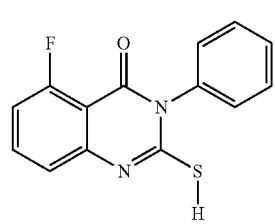 [SMILES: O=c1c2c(F)cccc2nc(S)n1-c1ccccc1]

The title compound was prepared from the reaction of 2-amino-6-fluoro benzoic acid with phenylthioisocyante according to the general procedure A. Obtained as a white solid MS (EI) 273 [(M+1)+].

Example A8

3-(3-fluoro-4-chlorophenyl)-5-fluoro-2-mercaptoquinazolin-4(3H)-one

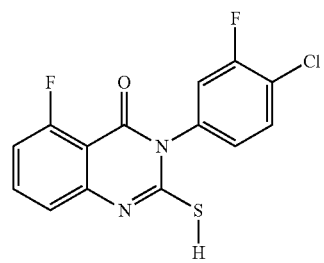

The title compound was prepared from the reaction of 2-amino-6-fluoro benzoic acid with 3-fluoro-4-chlorophenylthioisocyante according to the general procedure A. Obtained as a white solid MS (EI) 325[(M+1)+].

Example A9

3-(3,4-di chlorophenyl)-5-fluoro-2-mercaptoquinazolin-4(3H)-one

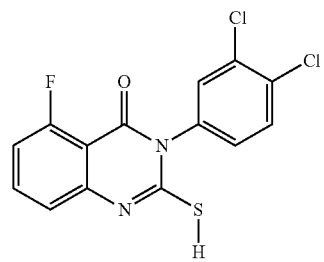 [SMILES: O=c1c2c(F)cccc2nc(S)n1-c1ccc(Cl)c(F)c1]

The title compound was prepared from the reaction of 2-Amino-6-fluoro benzoic acid with 3,4-dichlorophenylthioisocyante according to the general procedure A. Obtained as a white solid MS (EI) 340[(M+1)+].

Example A10

3-(3-fluoro-4-bromophenyl)-5-fluoro-2-mercaptoquinazolin-4(3H)-one

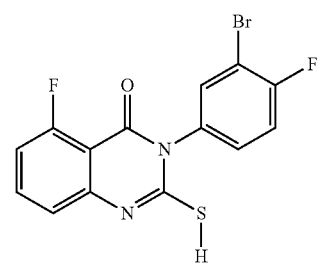 [SMILES: O=c1c2c(F)cccc2nc(S)n1-c1ccc(F)c(Br)c1]

The title compound was prepared from the reaction of 2-amino-6-fluoro benzoic acid with 3-bromo-4-fluorophenylthioisocyante according to the general procedure A. Obtained as a white solid MS (EI) 340[(M+1)+].

Examples B

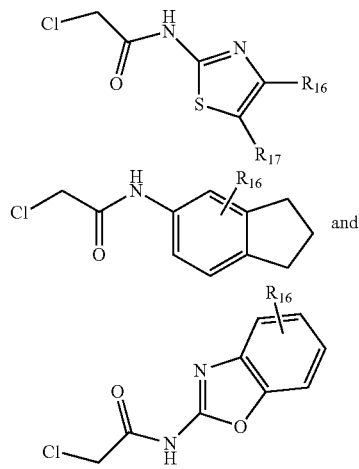

General Procedure B

Example B1

2-chloro-N-(2,3-Dihydro-1H-inden-5-yl)acetamide

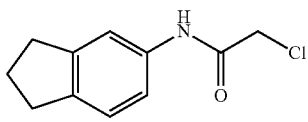 [SMILES: O=C(CCl)Nc1ccc2c(c1)CCC2]

2,3-Dihydro-1H-inden-5-amine (13.32 g, 0.01 mole), 15 mL of triethylamine were added to 200 mL of dichloromethane in a 500 mL round bottom flask. The flask was cooled to 0° C. and chloroacetyl chloride (11.12 g, 0.01 mole) in 50 mL of dichloromethane was slowly added. The reaction was warmed to room temperature and stirred overnight. The mixture was evaporated under vacuum and the residue was dissolved in 200 mL of ethyl acetate and 100 mL of water. The organic layer was washed successively with NaHCO₃, 10% citric acid, brine and dried over sodium sulfate and the organic layer was evaporated under vacuum to afford as a white solid 2.1 g (98% yield) of the target compound 2-Chloro-N-(2,3-dihydro-1H-inden-5-yl) acetamide. 1H NMR (400 MHz, DMSO-d6) δ 1.95 (m, 2H), 2.80 (m, 4H), 4.24 (s, 3H), 7.18-7.31 (m, 2H), 7.58 (m, 1H), MS (EI) 210[(M+1)+].

Example B2

2-chloro-N-(2,3-dihydro-1H-inden-1-yl)acetamide

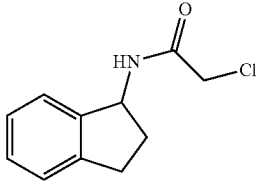 [SMILES: O=C(CCl)NC1CCc2ccccc21]

The title compound was prepared from the reaction of 2,3-dihydro-1H-inden-1-amine with chloroacetyl chloride according to the general procedure B. Obtained as a white solid MS (EI) 210[(M+1)+].

Example B3

N-(benzo[d](1,3)dioxol-5-yl-2-chloroacetamide

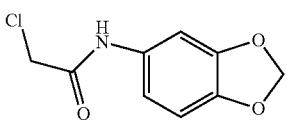 [SMILES: O=C(CCl)Nc1ccc2c(c1)OCO2]

The title compound was prepared from the reaction of benzo[d](1,3)dioxol-5-amine with chloroacetyl chloride according to the general procedure B. Obtained as a white solid MS (EI) 214[(M+1)+].

Example B4

5-chloro-N-(2,3-dihydro-1H-inden-5-yl)pentanamide

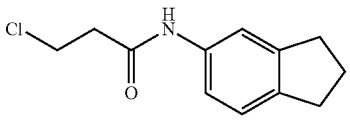 [SMILES: O=C(CCCl)Nc1ccc2c(c1)CCC2]

The title compound was prepared from the reaction of 2,3-dihydro-1H-inden-5-amine with 3-chloropropanoyl chloride according to the general procedure B. Obtained as a white solid MS (EI) 224[(M+1)+].

Example B5

4-Chloro-N-(2,3-dihydro-1H-indene-5-yl)butanamide

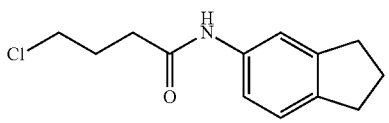 [SMILES: O=C(CCCCl)Nc1ccc2c(c1)CCC2]

The title compound was prepared from the reaction of 2,3-dihydro-1H-inden-5-amine with 4-chlorobutanoyl chloride according to the general procedure B. Obtained as a white solid MS (EI) 238[(M+1)+].

Example B6

5-chloro-N-(2,3-dihydro-1H-inden-5-yl)pentanamide

The title compound was prepared from the reaction of 2,3-dihydro-1H-inden-5-amine with 4-chloropentanoyl chloride according to the general procedure B. Obtained as a white solid MS (EI) 252[(M+1)+].

Example B7

2-Chloro-N-(5-chlorobenzo[d]oxazol-2-yl)acetamide

The title compound was prepared from the reaction of 5-chlorobenzo[d]oxazol-2-amine with chloroacetyl chloride according to the general procedure B. Obtained as a white solid MS (EI) 245[(M+1)+].

Example B8

N-Benzoyl[d]thiazol-6-yl)-2-chloroacetamide

The title compound was prepared from the reaction of benzo[d]thiazol-6-amine with chloroacetyl chloride according to the general procedure B. Obtained as a white solid MS (EI) 228[(M+1)+].

Example B9

2-Chloro-N-(phenylthiazol-20yl)acetamide

The title compound was prepared from the reaction of 4-phenylthiazol-2-amine with chloroacetyl chloride according to the general procedure B. Obtained as a white solid MS (EI) 253[(M+1)+].

Example B10

2-Chloro-N-(methylthiazol-2-yl)acetamide

The title compound was prepared from the reaction of 4-methylthiazol-2-amine with chloroacetyl chloride according to the general procedure B. Obtained as a white solid MS (EI) 191[(M+1)+].

Examples C

General Procedure C

Example C1

N-(2,3-dihydro-1H-inden-5-yl)-2-(4-oxo-3-phenyl-3, 4-dihydroquinazolin-2-yl)thio) acetamide 2-Mercapto-3-phenylquinazolin-4(3H)-one (659.5 mg, 2.96 mmol), 2-chloro-N-(2,3-dihydro-1H-inden-5-yl) acetamide (620.6 mg, 2.96 mmol), sodium acetate (848.6 mg, 10.36 mmol) and 6 mL of dioxane were placed in a 50 ml round bottom flask. The reaction mixture was heated to reflux overnight. The solvent was removed under reduced pressure and the residue was dissolved in 50 mL of dichloromethane and 50 mL of water. The organic layers were separated and washed successively with 50 mL of saturated sodium bicarbonate, 1N hydrochloric acid and the organic layer was dried over sodium sulfate, filtered and evaporated under reduced pressure. The residue was crystallized from ethanol to afford fine brown needles 400 mg (30% yield) of the target compound N-(2,3-dihydro-1H-inden-5-yl)-2-(4-oxo-3-phenyl-3,4-dihydroquinazolin-2-yl)thio) acetamide 1H NMR (400 MHz, DMSO-d6) δ 1.95 (m, 2H), 2.80 (m, 4H), 4.04 (s, 3H), 7.09 (d, J=7.1 Hz, 1H), 7.21 (d, 3=7.1 Hz, 1H), 7.40-7.62 (m, 7H), 7.78 (d, 3=7.1 Hz, 1H), 8.06 (d, 3=7.1 Hz, 1H), 10.15 (s, 1H), MS (EI) 427 [(M+1)+].

Example C2

2-(3-(3,4-dichlorophenyl)-4-oxo-3,4-dihydroquinazolin-2-ylthio)-N-(2,3-dihydro-1H-inden-1-yl) acetamide

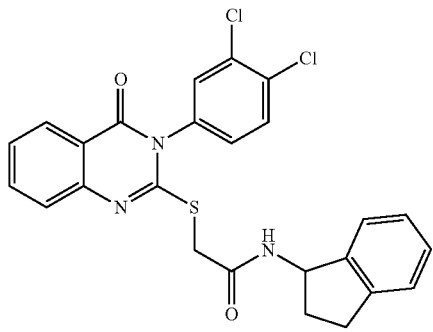 [SMILES: O=C(CSc1nc2ccccc2c(=O)n1-c1ccc(Cl)c(Cl)c1)NC1CCc2ccccc21]

The title compound was prepared from the reaction of 3-(3,4-dichlorophenyl)-2-mercaptoquinazolin-4(3H)-one with 2-chloro-N-(2,3-dihydro-1H-inden-1-yl) acetamide according to the general procedure C. Obtained as a white solid MS (D) 497[(M+1)+].

Example C3

2-(3-(3-chloro-4-fluorophenyl)-4-oxo-3,4-dihydroquinazolin-2-ylthio)-N-(2,3-dihydro-1H-inden-5-yl) acetamide

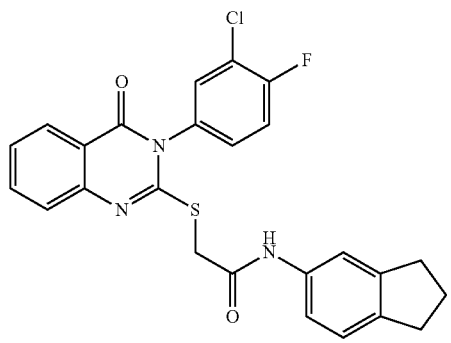 [SMILES: O=C(CSc1nc2ccccc2c(=O)n1-c1ccc(F)c(Cl)c1)Nc1ccc2c(c1)CCC2]

The title compound was prepared from the reaction of 3-(3-chloro-4-fluorophenyl)-2-mercaptoquinazolin-4(3H)-one with 2-chloro-N-(2,3-dihydro-1H-inden-5-yl)acetamide according to the general procedure C. Obtained as a white solid MS (D) 480[(M+1)+].

Example C4

5-(3-(3-chloro-4-fluorophenyl)-4-oxo-3,4-dihydroquinazolin-2-ylthio)-N-(2,3-dihydro-1H-inden-5-yl) pentanamide

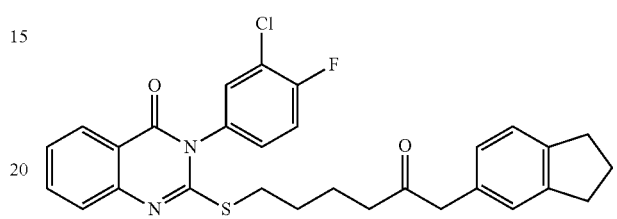

The title compound was prepared from the reaction of 3-(3-chloro-4-fluorophenyl)-2-mercaptoquinazolin-4(3H)-one with 5-chloro-N-(2,3-dihydro-1H-inden-5-yl)pentanamide according to the general procedure C. Obtained as a white solid MS (D) 522[(M+1)+].

Example C5

N-(5-chlorobenzo[d]oxazol-2-yl)-2-(3-(3,4-dichlorophenyl)-4-oxo-3,4-dihydroquinazolin-2-ylthio)acetamide

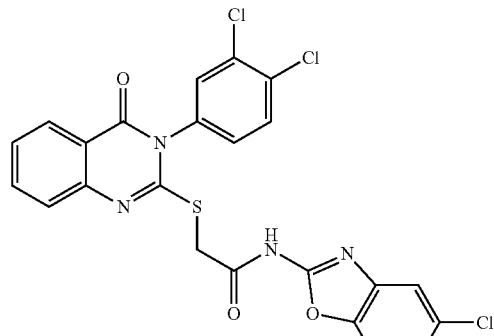

The title compound was prepared from the reaction of 3-(3,4-dichlorophenyl)-2-mercaptoquinazolin-4(3H)-one with 3-chloro-N-(5-chlorobenzo[d]oxazol-2-yl)propanamide according to the general procedure C. Obtained as a white solid MS (EI) 531 [(M+1)+].

Example C6

N-(benzo[d]thiazol-6-yl)-2-(3-(3,4-dichlorophenyl)-4-oxo-3,4-dihydroquinazolin-2-ylthio)acetamide

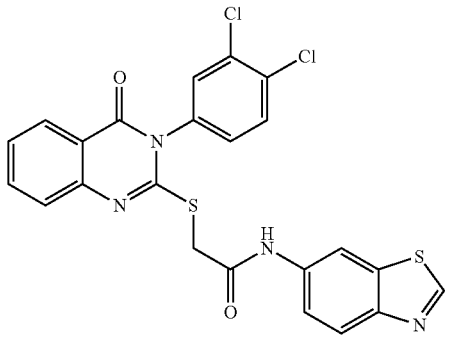 [SMILES: O=C(CSc1nc2ccccc2c(=O)n1-c1ccc(Cl)c(Cl)c1)Nc1ccc2ncsc2c1]

The title compound was prepared from the reaction of 3-(3,4-dichlorophenyl)-2-mercaptoquinazolin-4(3H)-one with N-(benzo[d]thiazol-6-yl)-2-chloroacetamide according to the general procedure C. Obtained as a white solid MS (EI) 513[(M+1)+].

Example C7

2-(3-(3,4-dichlorophenyl)-4-oxo-3,4-dihydroquinazolin-2-ylthio)-N-(4-phenylthiazol-2-yl)acetamide compound with N-(benzo[d]thiazol-6-yl)-2-chloroacetamide (1:1)

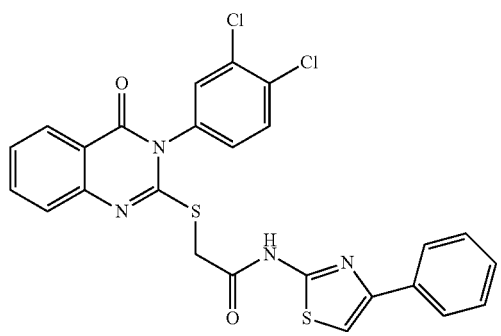 [SMILES: O=C(CSc1nc2ccccc2c(=O)n1-c1ccc(Cl)c(Cl)c1)Nc1nc(-c2ccccc2)cs1]

The title compound was prepared from the reaction of 3-(3,4-dichlorophenyl)-2-mercaptoquinazolin-4(3H)-one with 2-chloro-N-(4-phenylthiazol-2-yl)acetamide to the general procedure C. Obtained as a white solid MS (EI) 513[(M+1)+].

Example C8

2-(3-(3,4-dichlorophenyl)-4-oxo-3,4-dihydroquinazolin-2-ylthio)-N-(4-methylthiazol-2-yl)acetamide

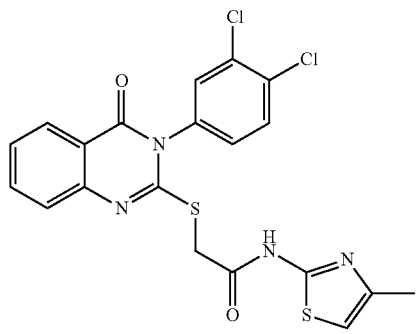 [SMILES: Cc1csc(NC(=O)CSc2nc3ccccc3c(=O)n2-c2ccc(Cl)c(Cl)c2)n1]

The title compound was prepared from the reaction of 3-(3,4-dichlorophenyl)-2-mercaptoquinazolin-4(3H)-one with 2-chloro-N-(4-methylthiazol-2-yl)acetamide to the general procedure C. Obtained as a white solid MS (EI) 478[(M+1)+].

Example C9

N-(2,3-dihydro-1H-inden-5-yl)-5-(4-oxo-3-(3,4,5-trifluorophenyl)-3,4-dihydroquinazolin-2-ylthio)pentanamide

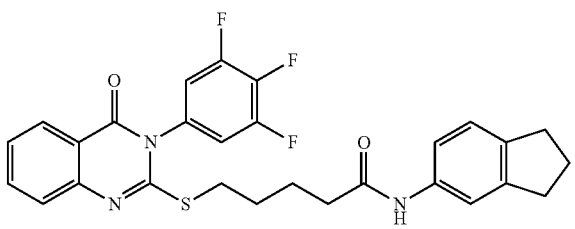 [SMILES: O=C(CCCCSc1nc2ccccc2c(=O)n1-c1cc(F)c(F)c(F)c1)Nc1ccc2c(c1)CCC2]

The title compound was prepared from the reaction of 3-(3,4,5-trifluorophenyl)-2-mercaptoquinazolin-4(3H)-one with 5-chloro-N-(2,3-dihydro-1H-inden-5-yl)pentanamide according to the general procedure C. Obtained as a white solid MS (EI) 524[(M+1)+].

Example C10

N-(2,3-dihydro-1H-inden-5-yl)-5-(5-fluoro-4-oxo-3-phenyl-3,4-dihydroquinazolin-2-ylthio)pentanamide

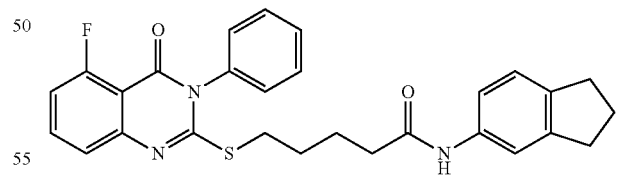

The title compound was prepared from the reaction of 5-fluoro-2-mercapto-3-phenylquinazolin-4(3H)-one with 5-chloro-N-(2,3-dihydro-1H-inden-5-yl)pentanamide according to the general procedure C. Obtained as a white solid MS (EI) 524[(M+1)+].

The following compounds were synthesized using the procedures described above in the general procedure A, B, and C sections.

| Compound | Name | MS (EI) [(M + 1)+]* |
|---|---|---|
| C11 | 2-[3-(2-fluorophenyl)-4-oxo(3-hydroquinazolin-2-ylthio)]-N-indan-5-ylacetamide | 446 |
| C12 | 2-[3-(3-chloro-4-fluorophenyl)-4-oxo(3-hydroquinazolin-2-ylthio)]-N-indan-5-ylacetamide | 481 |
| C13 | 2-[3-(3,4-dichlorophenyl)-4-oxo(3-hydroquinazolin-2-ylthio)]-N-indan-5-ylacetamide | 497 |
| C14 | 2-(6-fluoro-4-oxo-3-phenyl(3-hydroquinazolin-2-ylthio))-N-indan-5-ylacetamide | 446 |
| C15 | 2-(5-fluoro-4-oxo-3-phenyl(3-hydroquinazolin-2-ylthio))-N-indan-5-ylacetamide | 446 |
| C16 | N-indan-5-yl-2-(8-methyl-4-oxo-3-phenyl(3-hydroquinazolin-2-ylthio))acetamide | 442 |
| C17 | N-indan-5-yl-2-(8-methoxy-4-oxo-3-phenyl(3-hydroquinazolin-2-ylthio))acetamide | 458 |
| C18 | 2-[3-(3,4-dichlorophenyl)-4-oxo(3-hydroquinazolin-2-ylthio)]-N-indan-4-ylacetamide | 497 |
| C19 | N-(2H-benzo[d]1,3-dioxolen-5-yl)-2-[3-(3,4-dichlorophenyl)-4-oxo(3-hydroquinazolin-2-ylthio)]acetamide | 501 |
| C20 | 2-[3-(3,5-dichlorophenyl)-4-oxo(3-hydroquinazolin-2-ylthio)]-N-indan-5-ylacetamide | 497 |
| C21 | 3-[3-(3-chloro-4-fluorophenyl)-4-oxo(3-hydroquinazolin-2-ylthio)]-N-indan-5-ylpropanamide | 494 |
| C22 | 2-[3-(3-chloro-4-fluorophenyl)-4-oxo(3-hydroquinazolin-2-ylthio)]-N-indan-4-ylacetamide | 481 |
| C23 | N-(2H-benzo [3,4-d]1,3-dioxolan-5-yl)-2-[3-(3-chloro-4-fluorophenyl)-4-oxo(3-hydroquinazolin-2-ylthio)]acetamide | 485 |
| C24 | 2-[3-(3,4-dichlorophenyl)-4-oxo(3-hydroquinazolin-2-ylthio)]-N-(4-methyl(1,3-thiazol-2-yl))acetamide | 478 |
| C25 | N-indan-5-yl-3-[4-oxo-3-(3,4,5-trifluorophenyl)(3-hydroquinazolin-2-ylthio)]propanamide | 497 |
| C26 | 2-[3-(3,4-difluorophenyl)-4-oxo(3-hydroquinazolin-2-ylthio)]-N-indan-4-ylacetamide | 543 |
| C27 | 2-[3-(3,4-difluorophenyl)-4-oxo(3-hydroquinazolin-2-ylthio)]-N-indan-5-ylacetamide | 464 |
| C28 | 2-(5-fluoro-4-oxo-3-phenyl(3-hydroquinazolin-2-ylthio))-N-(1,2,3,4-tetrahydronaphthyl)acetamide | 460 |
| C29 | 2-[3-(4-chloro-3-fluorophenyl)-5-fluoro-4-oxo(3-hydroquinazolin-2-ylthio)]-N-indan-5-ylacetamide | 499 |
| C30 | 2-[5-fluoro-4-oxo-3-(3,4,5-trifluorophenyl)(3-hydroquinazolin-2-ylthio)]-N-indan-5-ylacetamide | 524 |
| C31 | 2-[3-(3,4-dichlorophenyl)-5-fluoro-4-oxo(3-hydroquinazolin-2-ylthio)]-N-indan-5-ylacetamide | 515 |
| C32 | N-indan-5-yl-2-(4-oxo-3-phenyl(3-hydroquinazolin-2-ylthio))acetamide | 428 |
| C33 | 2-[3-(4-chloro-3-methylphenyl)-4-oxo(3-hydroquinazolin-2-ylthio)]-N-indan-5-ylacetamide | 477 |
| C34 | 2-[3-(4-fluoro-3-methylphenyl)-4-oxo(3-hydroquinazolin-2-ylthio)]-N-indan-5-ylacetamide | 460 |
| C35 | N-indan-5-yl-2-[4-oxo-3-(3,4,5-trifluorophenyl)(3-hydroquinazolin-2-ylthio)]acetamide | 482 |
| C36 | 2-[3-(3-bromo-4-methylphenyl)-4-oxo(3-hydroquinazolin-2-ylthio)]-N-indan-5-ylacetamide | 521 |
| C37 | 2-[3-(3,4-dichlorophenyl)-8-fluoro-4-oxo(3-hydroquinazolin-2-ylthio)]-N-indan-5-ylacetamide | 515 |
| C38 | 2-[3-(3,5-difluorophenyl)-4-oxo(3-hydroquinazolin-2-ylthio)]-N-indan-5-ylacetamide | 464 |
| C39 | 2-[3-(3,5-dichlorophenyl)-8-fluoro-4-oxo(3-hydroquinazolin-2-ylthio)]-N-indan-5-ylacetamide | 515 |
| C40 | 2-[3-(2,6-dichlorophenyl)-4-oxo(3-hydroquinazolin-2-ylthio)]-N-indan-5-ylacetamide | 497 |
| C41 | 2-[3-(3-bromo-4-chlorophenyl)-4-oxo(3-hydroquinazolin-2-ylthio)]-N-indan-5-ylacetamide | 542 |
| C42 | 2-(8-fluoro-4-oxo-3-phenyl(3-hydroquinazolin-2-ylthio))-N-indan-5-ylacetamide | 446 |
| C43 | 2-[3-(4,5-difluoro(2-pyridyl))-4-oxo(3-hydroquinazolin-2-ylthio)]-N-indan-5-ylacetamide | 465 |
| C44 | 2-[3-(4-chloro-5-fluoro(2-pyridyl))-4-oxo(3-hydroquinazolin-2-ylthio)]-N-indan-5-ylacetamide | 482 |
| C45 | 2-[3-(3,4-dichlorophenyl)-4-oxo(3-hydroquinazolin-2-ylthio)]-N-(4-phenyl(1,3-thiazol-2-yl))acetamide | 540 |
| C46 | N-benzothiazol-5-yl-2-[3-(3,4-dichlorophenyl)-4-oxo(3-hydroquinazolin-2-ylthio)]acetamide | 514 |

*MS (E1) [(M + 1)+]" is the molecular mass as determined by mass spectrometry used to confirm the structure of each compound.

Other compounds employed according to the present invention can be prepared as shown above by employing a corresponding substituted 2-amino benzoic acid and corresponding substituted phenylthioisocynate. In addition, compounds employed according to the present disclosure can be prepared using the methods disclosed in WO 2005/049613 to Bayliss et al., disclosure of which is incorporated herein by reference using the appropriate reactants.

The following tables show results obtained from testing of compounds according to the present disclosure.

TABLE 1

| Example | HCV Con 1b (Replicon) RNA end-point | | |
|---|---|---|---|
| | $IC_{50}$ (μM) | $TC_{50}$ (μM) | $TI_{50}$ |
| C1 | C | A | C |
| C12 | A | B | A |
| C15 | B | A | B |
| C26 | A | B | C |
| C45 | A | B | B |

$IC_{50}$: A <1.0 μM; B 1-5 μM; C >5 and <25 μM
$TC_{50}$: A ≥100.0 μM; B <100-≥50 μM; C <50-≥10 μM; D <10 μM
$TI_{50}$: A ≥50; B <50-≥10; C <10-≥5; D <5

TABLE 2

| Example | JEV | | |
|---|---|---|---|
| | $IC_{50}$ (μM) | $TC_{50}$ (μM) | $TI_{50}$ |
| C8 | C | A | C |
| C15 | C | A | B |
| C17 | C | A | C |
| C24 | C | A | C |
| C25 | C | A | C |

$IC_{50}$: A <1.0 μM; B 1-5 μM; C >5 and <25 μM
$TC_{50}$: A ≥100.0 μM; B <100-≥50 μM; C <50-≥10 μM; D <10 μM
$TI_{50}$: A ≥50; B <50-≥10; C <10-≥5; D <5

TABLE 3

| Example | HCV Con1b (Replicon) Luciferase end-point | | |
|---|---|---|---|
| | $IC_{50}$ (μM) | $TC_{50}$ (μM) | $TI_{50}$ |
| C8 | B | A | B |
| C12 | B | A | A |
| C13 | B | B | C |
| C16 | B | C | B |
| C17 | B | A | B |
| C18 | C | B | B |
| C19 | B | A | B |
| C21 | C | C | C |
| C22 | B | C | C |
| C23 | C | A | C |
| C24 | B | A | B |
| C26 | A | A | A |
| C27 | C | A | B |
| C28 | C | A | C |
| C29 | B | A | A |
| C30 | B | B | B |
| C31 | A | C | A |
| C45 | A | A | A |
| C46 | B | A | B |

$IC_{50}$: A <1.0 μM; B 1-5 μM; C >5 and <25 μM
$TC_{50}$: A ≥100.0 μM; B <100-≥50 μM; C <50-≥10 μM; D <10 μM
$TI_{50}$: A ≥50; B <50-≥10; C <10-≥5; D <5

TABLE 4

| Example | WNV | | |
|---|---|---|---|
| | $IC_{50}$ (μM) | $TC_{50}$ (μM) | $TI_{50}$ |
| C1 | C | A | C |
| C11 | C | A | C |
| C12 | C | A | B |
| C13 | C | A | B |
| C20 | B | A | B |
| C27 | C | A | B |
| C31 | C | A | C |
| C32 | C | A | B |
| C33 | B | B | B |
| C34 | C | A | B |
| C35 | C | A | B |
| C36 | C | A | B |
| C37 | C | C | C |
| C38 | C | A | C |
| C39 | C | B | C |
| C40 | C | A | C |
| C41 | C | A | C |
| C42 | C | A | C |
| C43 | C | A | C |

$IC_{50}$: A <1.0 μM; B 1-5 μM; C >5 and <25 μM
$TC_{50}$: A ≥100.0 μM; B <100-≥50 μM; C <50-≥10 μM; D <10 μM
$TI_{50}$: A ≥50; B <50-≥10; C <10-≥5; D <5

The use of N-(2,3-dihydro-1H-inden-5-yl)-2-(4-oxo-3-phenyl-3,4-dihydro-quinazolin-2-yl)thio) acetamide, a compound employed according to the present disclosure, for treating West Nile Virus has been disclosed. For example, please see Chung et al. *A Cell Based Assay for the Identification of Lead Compounds with Anti-Viral Activity Against West Nile Virus*, Probe Reports from the NIH Molecular Libraries Program [Internet]. Bethesda (Md.): National Center for Biotechnology Information (US); 2010-2010 Feb. 27 [updated 2010 Oct. 4], PMID: 21433390 [PubMed]. When N-(2,3-dihydro-1H-inden-5-yl)-2-(4-oxo-3-phenyl-3,4-dihydroquinazolin-2-yl)thio) acetamide was tested against Hepatitis C Virus, activity was observed (Table 1). Testing analogs of N-(2,3-dihydro-1H-inden-5-yl)-2-(4-oxo-3-phenyl-3,4-dihydroquinazolin-2-yl)thio) acetamide in cell based virus CPE reduction assays showed Japanese Encephalitis Virus replication was also inhibited by analogs of N-(2,3-dihydro-1H-inden-5-yl)-2-(4-oxo-3-phenyl-3,4-dihydroquinazolin-2-yl)thio) acetamide (Table 2).

Compounds according to the present disclosure can be used in treating Hepatitis C Virus (genotypes 1-7) (Table 1 and Table 3) and Japanese Encephalitis Virus (Table 2). In addition certain compounds according to the present disclosure can be used in treating West Nile Virus (Table 4).

The reduction in HCV was determined with two assays using viral RNA endpoints. A qPCR analysis and a blot hydridization method were used to show that the activity is specific for HCV and not the luciferase end-point (Table 4). The data demonstrated activity in a cell based HCV replicon assay (con 1b). This cell line expresses a subgenomic section of the HCV genome containing NS2a, NS2b, NS3a, NS3b, NS4a, NS4b, NS5a and NS5b. However, no activity was observed in biochemical assays: HCV protease (NS3b), HCV helicase, WNV protease (NS2bNS3), and HCV polymerase (NS5b), these data exclude these proteins as targets of the quinazolinone activity.

Exemplary embodiments of the present disclosure include:

Embodiment 1: A process for treating or preventing a viral infection in a subject, wherein said viral infection is from a flavivirus selected from the group consisting of Hepatitis C Virus (genotypes 1-7) and Japanese Encephalitis Virus, which comprises administering to said subject a therapeutically effective amount of at least one compound represented by the formula:

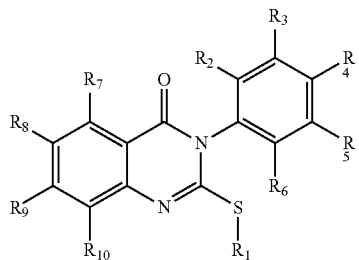

wherein $R_1$ is represented by the formula:

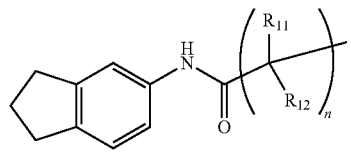

and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, formyl, $CF_3$, $S(C_{1-4}$ alkyl), $S(O)C_{1-4}$ alkyl, $S(O)_2C_{1-4}$alkyl, $C_{1-4}$alkylcarbonyl, $C_{1-6}$alkyl, hydroxy $C_{1-6}$alkyl, $C_{1-6}$alkoxy, halo$C_{1-6}$alkoxy, hydroxy $C_{1-6}$ alkoxy, $C_{2-6}$alkenyl, $C_{2-6}$alkynyl, $C_{1-6}$alkylamino, di($C_{1-6}$alkyl)amino; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof.

Embodiment 2: A process for treating or preventing a viral infection in a subject, wherein said viral infection is from a flavivirus selected from the group consisting of Hepatitis C Virus (genotypes 1-7) and Japanese Encephalitis Virus, which comprises administering to said subject a therapeutically effective amount of at least one compound represented by the formula:

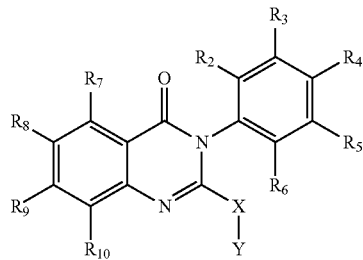

wherein X is O, S or $NR_{20}$ wherein $R_{20}$ is H or $C_{1-6}$alkyl;
Y is $(CR_{11}CR_{12})_n(CO)_pNR_{13}W$;

$R_{11}$ and $R_{12}$ are independently selected from the group consisting of H, halogen, hydroxyl, $C_{1-6}$alkoxy, amino, nitro, cyano, $CF_3$ and $C_{1-4}$alkyl;

$R_{13}$ is H or $C_{1-6}$alkyl;
n is zero, one, two, three, four, five or six;
p is zero or one;
W is hydrogen, $C_{1-6}$alkoxy, halo $C_{1-6}$alkoxy, $C_{1-6}$alkyl, halo $C_{1-6}$alkyl, hydroxy$C_{1-6}$alkyl, amino $C_{1-6}$alkyl, carboxy$C_{1-6}$alkyl, $C_{3-7}$cycloalkyl, halo $C_{3-7}$cycloalkyl; or a substituted or unsubstituted phenyl ring, a substituted or unsubstituted five- or 6-membered saturated or unsaturated heterocyclic ring containing one, two, three or four heteroatoms independently chosen from O, N and S, or a nine- or ten- or eleven-membered fused bicyclic ring containing a phenyl ring or a six-membered heteroaromatic ring as just defined, fused to either a saturated or unsaturated five- or six- or seven-membered ring, which can be substituted or unsubstituted, when substituted any of the above rings can be substituted by halogen, $C_{1-6}$alkyl, $C_{2-6}$alkenyl, $C_{2-6}$alkynyl, nitro, cyano, $C_{3-7}$cycloalkyl, hydroxy, $C_{1-6}$alkoxy, halo$C_{1-6}$alkyl, halo $C_{1-6}$alkoxy, hydroxy $C_{1-6}$alkyl, hydroxy $C_{1-6}$alkoxy, phenyl, an unsubstituted five-membered heteroaromatic ring as just described, a six-membered heteroaromatic ring as just described, a six-membered saturated ring as just described or $NR_{14}R_{15}$; each $R_{14}$ and $R_{15}$ is independently hydrogen or $C_{1-6}$alkyl or $R_{14}$ and $R_{15}$, together with the nitrogen atom to which they are attached, may form a saturated 4-7 membered ring; and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, formyl, $CF_3$, $S(C_{1-4}$ alkyl), $S(O)C_{1-4}$ alkyl, $S(O)_2C_{1-4}$alkyl, $C_{1-4}$alkylcarbonyl, $C_{1-6}$alkyl, hydroxy $C_{1-6}$alkyl, $C_{1-6}$alkoxy, halo$C_{1-6}$alkoxy, hydroxy $C_{1-6}$ alkoxy, $C_{2-6}$alkenyl, $C_{2-6}$alkynyl, $C_{1-6}$alkylamino, di($C_{1-6}$alkyl)amino; pharmaceutically acceptable salts thereof; solvates thereof and deuterated forms thereof Embodiment 3: The process according to Embodiment 2 wherein Y in the above formula is $X(C_2H_2)C(=O)NH$ and W is a member selected from the group consisting of

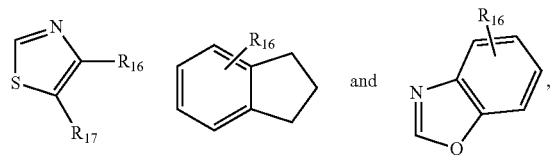

wherein $R_{16}$ and $R_{17}$ each is independently selected from the group consisting of H, halo, alkyl, alkoxy and aryl or $R_{16}$ and $R_{17}$ can be attached to form a five, six or seven membered ring, that can be substituted or unsubstituted and wherein the ring can be a hetero ring containing one or more O, S and/or N hetero atoms in the ring.

Embodiment 4: The process according to any one of embodiments 2 or 3 wherein W is a member selected from the group consisting of:

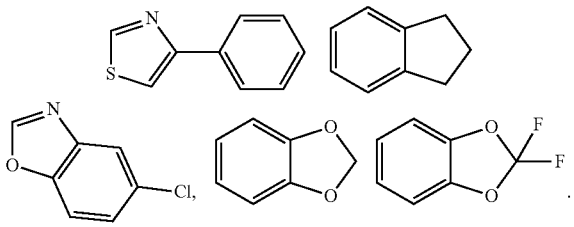

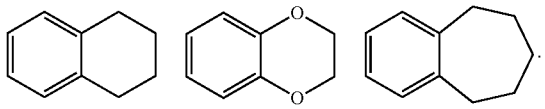

Embodiment 5: The process according to any one of embodiments 1 to 4, wherein said alkyl and said alkoxy contain 1 to 4 carbon atoms.

Embodiment 6: The process according to any one of embodiments 1 to 5, wherein each of $R_2$, $R_4$, $R_5$, $R_6$, $R_7$, $R_8$, $R_9$ and $R_{10}$ is H and $R_3$ is F.

Embodiment 7: The process according to any one of embodiments 1 to 5, wherein each of $R_2$, $R_5$, $R_6$, $R_7$, $R_8$, $R_9$ and $R_{10}$ is H, $R_3$ is Cl and $R_4$ is F.

Embodiment 8: The process according to any one of embodiments 1 to 5, wherein each of $R_2$, $R_5$, $R_6$, $R_7$, $R_8$, $R_9$ and $R_{10}$ is H and $R_3$ and $R_4$ are each Cl.

Embodiment 9: The process according to any one of embodiments 1 to 5, wherein each of $R_2$, $R_3$, $R_5$, $R_6$, $R_7$, $R_8$, $R_9$ and $R_{10}$ is H and $R_4$ is F.

Embodiment 10: The process according to any one of embodiments 1 to 5, wherein each of $R_2$, $R_3$, $R_4$, $R_5$, $R_6$, $R_7$, $R_9$ and $R_{10}$ is H and $R_8$ is F.

Embodiment 11: The process according to any one of embodiments 1 to 5, wherein each of $R_2$, $R_3$, $R_4$, $R_5$, $R_6$, $R_7$, $R_9$ and $R_{10}$ is H and $R_8$ is $CH_3$.

Embodiment 12: The process according to any one of embodiments 1 to 5, wherein each OF $R_2$, $R_3$, $R_4$, $R_5$, $R_6$, $R_8$, $R_9$ and $R_{10}$ is H and $R_7$ is F.

Embodiment 13: The process according to any one of embodiments 1 to 5, wherein each of $R_2$, $R_3$, $R_4$, $R_5$, $R_6$, $R_8$, $R_9$ and $R_{10}$ is H and $R_7$ is I.

Embodiment 14: The process according to any one of embodiments 1 to 5, wherein each of $R_2$, $R_3$, $R_4$, $R_5$, $R_6$, $R_7$, $R_8$ and $R_9$ is H and $R_{10}$ is $CH_3$.

Embodiment 15: The process according to any one of embodiments 1 to 5, wherein each of $R_2$, $R_3$, $R_4$, $R_5$, $R_6$, $R_7$, $R_8$ and $R_9$ is H and $R_{10}$ is $OCH_3$.

Embodiment 16: The process according to any one of embodiments 1 to 5, wherein each of $R_2$, $R_4$, $R_6$, $R_7$, $R_8$, $R_9$ and $R_{10}$ is H and each of $R_3$ and $R_5$ is Cl.

Embodiment 17: The process according to any one of embodiments 1 to 5, wherein each of $R_2$, $R_6$, $R_7$, $R_8$, $R_9$ and $R_{10}$ is H and each of $R_3$, $R_4$ and $R_5$ is F.

Embodiment 18: The process according to any one of embodiments 1 to 5, wherein each of $R_2$, $R_3$, $R_4$, $R_5$, $R_6$, $R_8$, $R_9$ and $R_{10}$ is H and $R_7$ is F.

Embodiment 19: The process according to any one of embodiments 1 to 5, wherein each of $R_2$, $R_5$, $R_6$, $R_8$, $R_9$ and $R_{10}$ is H and each of $R_3$ and $R_7$ is F and $R_4$ is Cl.

Embodiment 20: The process according to any one of embodiments 1 to 5, wherein each of $R_2$, $R_3$, $R_6$, $R_8$, $R_9$ and $R_{10}$ is H and each of $R_4$, $R_5$ and $R_7$ is F.

Embodiment 21: The process according to any one of embodiments 1 to 5, wherein each of $R_2$, $R_5$, $R_6$, $R_8$, $R_9$ and $R_{10}$ is H and each of $R_3$, $R_4$ and $R_7$ is F.

Embodiment 22: The process according to any one of embodiments 1 to 5 wherein each of each $R_2$, $R_6$, $R_8$, $R_9$ and $R_{10}$ is H and each of $R_3$, $R_4$, $R_5$ and $R_7$ is F.

Embodiment 23: The process according to any one of embodiments 1 to 5, wherein each $R_2$, $R_3$, $R_6$, $R_8$, $R_9$ and $R_{10}$ is H, each of $R_4$ and $R_5$ is Cl and $R_7$ is F.

Embodiment 24: The process according to any one of embodiments 1 to 5, wherein each $R_2$, $R_5$, $R_6$, $R_8$, $R_9$ and $R_{10}$ is H, each of $R_3$ and $R_4$ is Cl and $R_7$ is F.

Embodiment 25: The process according to any one of embodiments 1 to 5, wherein each $R_2$, $R_3$, $R_6$, $R_8$, $R_9$ and $R_{10}$ is H, $R_5$ is Br and each of $R_4$ and $R_7$ is F.

Embodiment 26: The process according to any one of embodiments 1 to 5, wherein each $R_2$, $R_4$, $R_6$, $R_8$, $R_9$ and $R_{10}$ is H, $R_3$ is Br and each of $R_4$ and $R_7$ is F.

Embodiment 27: A process for treating or preventing a viral infection in a subject from Hepatitis C Virus, by administering to the subject a therapeutically effective amount of at least one compound selected from the group consisting of N-(2,3-dihydro-1H-inden-5-yl)-2-(4-oxo-3-phenyl-3,4-dihydroquinazolin-2-yl)thio) acetamide; 2-[3-(3-chloro-4-fluorophenyl)-4-oxo(3-hydroquinazolin-2-yl-thio)]-N-indan-5-ylacetamide; 2-[3-(3,4-dichlorophenyl)-4-oxo(3-hydroquinazolin-2-ylthio)]-N-indan-5-ylacetamide; 2-(5-fluoro-4-oxo-3-phenyl(3-hydroquinazolin-2-ylthio))-N-indan-5-ylacetamide; N-indan-5-yl-2-(8-methyl-4-oxo-3-phenyl(3-hydroquinazolin-2-ylthio))acetamide; N-indan-5-yl-2-(8-methoxy-4-oxo-3-phenyl(3-hydroquinazolin-2-ylthio))acetamide; 2-[3-(3,4-dichlorophenyl)-4-oxo(3-hydroquinazolin-2-ylthio)]-N-indan-4-ylacetamide; N-(2H-benzo[d]1,3-dioxolen-5-yl)-2-[3-(3,4-dichlorophenyl)-4-oxo(3-hydroquinazolin-2-ylthio)]acetamide; 3-[3-(3-chloro-4-fluorophenyl)-4-oxo(3-hydroquinazolin-2-ylthio)]-N-indan-5-ylpropanamide; 2-[3-(3-chloro-4-fluorophenyl)-4-oxo(3-hydroquinazolin-2-ylthio)]-N-indan-4-ylacetamide; N-(2H-benzo[3,4-d]1,3-dioxolan-5-yl)-2-[3-(3-chloro-4-fluorophenyl)-4-oxo(3-hydroquinazolin-2-ylthio)]acetamide; 2-[3-(3,4-dichlorophenyl)-4-oxo(3-hydroquinazolin-2-ylthio)]-N-(4-methyl(1,3-thiazol-2-yl))acetamide; 2-[3-(3,4-difluorophenyl)-4-oxo(3-hydroquinazolin-2-ylthio)]-N-indan-4-ylacetamide; 2-[3-(3,4-difluorophenyl)-4-oxo(3-hydroquinazolin-2-ylthio)]-N-indan-5-ylacetamide; 2-(5-fluoro-4-oxo-3-phenyl(3-hydroquinazolin-2-ylthio))-N-(1,2,3,4-tetrahydronaphthyl)acetamide; 2-[3-(4-chloro-3-fluorophenyl)-5-fluoro-4-oxo(3-hydroquinazolin-2-ylthio)]-N-indan-5-ylacetamide; 2-[5-fluoro-4-oxo-3-(3,4,5-trifluorophenyl)(3-hydroquinazolin-2-ylthio)]-N-indan-5-ylacetamide; 2-[3-(3,4-dichlorophenyl)-5-fluoro-4-oxo(3-hydroquinazolin-2-ylthio)]-N-indan-5-ylacetamide; 2-[3-(3,4-dichlorophenyl)-4-oxo(3-hydroquinazolin-2-ylthio)]-N-(4-phenyl(1,3-thiazol-2-yl))acetamide; and N-benzothiazol-5-yl-2-[3-(3,4-dichlorophenyl)-4-oxo(3-hydroquinazolin-2-ylthio)]acetamide; pharmaceutically acceptable salts thereof; solvates thereof and deuterated forms thereof.

Embodiment 28: A process for treating or preventing a viral infection in a subject from West Nile Virus by administering to the subject a therapeutically effective amount of at least one compound selected from the group consisting of: 2-[3-(2-fluorophenyl)-4-oxo(3-hydroquinazolin-2-ylthio)]-N-indan-5-ylacetamide; 2-[3-(3-chloro-4-fluorophenyl)-4-oxo(3-hydroquinazolin-2-ylthio)]-N-indan-5-ylacetamide; 2-[3-(3,4-dichlorophenyl)-4-oxo(3-hydroquinazolin-2-yl-thio)]-N-indan-5-ylacetamide; 2-[3-(3,5-dichlorophenyl)-4-oxo(3-hydroquinazolin-2-ylthio)]-N-indan-5-ylacetamide; 2-[3-(3,4-difluorophenyl)-4-oxo(3-hydroquinazolin-2-yl-thio)]-N-indan-5-ylacetamide, 2-[3-(3,4-dichlorophenyl)-5-fluoro-4-oxo(3-hydroquinazolin-2-ylthio)]-N-indan-5-ylacetamide; N-indan-5-yl-2-(4-oxo-3-phenyl(3-hydroquinazolin-2-ylthio))acetamide; 2-[3-(4-chloro-3-methylphenyl)-4-oxo(3-hydroquinazolin-2-ylthio)]-N-indan-5-ylacetamide; 2-[3-(4-fluoro-3-methylphenyl)-4-oxo(3-hydroquinazolin-2-ylthio)]-N-indan-5-ylacetamide; N-indan-5-yl-2-[4-oxo-3-(3,4,5-trifluorophenyl)(3-hydroquinazolin-2-ylthio)]acetamide; 2-[3-(3-bromo-4-methylphenyl)-4-oxo(3-hydroquinazolin-2-ylthio)]-N-indan-5-ylacetamide; 2-[3-(3,4-dichlorophenyl)-8-fluoro-4-oxo(3- hydroquinazolin-2-ylthio)]-N-indan-5-ylacetamide; 2-[3-(3, 5-difluorophenyl)-4-oxo(3-hydroquinazolin-2-ylthio)]-N-indan-5-ylacetamide; 2-[3-(3,5-dichlorophenyl)-8-fluoro-4-oxo(3-hydroquinazolin-2-ylthio)]-N-indan-5-ylacetamide; 2-[3-(2,6-dichlorophenyl)-4-oxo(3-hydroquinazolin-2-ylthio)]-N-indan-5-ylacetamide; 2-[3-(3-bromo-4-chlorophenyl)-4-oxo(3-hydroquinazolin-2-ylthio)]-N-indan-5-ylacetamide; 2-(8-fluoro-4-oxo-3-phenyl(3-hydroquinazolin-2-ylthio))-N-indan-5-ylacetamide; and 2-[3-(4,5-difluoro(2-pyridyl))-4-oxo(3-hydroquinazolin-2-ylthio)]-N-indan-5-ylacetamide; pharmaceutically acceptable salts thereof; solvates thereof and deuterated forms thereof.

Embodiment 29: A process for treating or preventing a viral infection in a subject from Japanese Encephalitis Virus by administering to the subject a therapeutically effective amount of at least one compound selected from the group consisting of 2-(5-fluoro-4-oxo-3-phenyl(3-hydroquinazolin-2-ylthio))-N-indan-5-ylacetamide; 2-[3-(3,4-dichlorophenyl)-4-oxo(3-hydroquinazolin-2-ylthio)]-N-indan-4-ylacetamide; 2-[3-(2,6-dichlorophenyl)-4-oxo(3-hydroquinazolin-2-ylthio)]-N-indan-5-ylacetamide; and 2-(8-fluoro-4-oxo-3-phenyl(3-hydroquinazolin-2-ylthio))-N-indan-5-ylacetamide; pharmaceutically acceptable salts thereof; solvates thereof and deuterated forms thereof.

Embodiment 30: A compound represented by the formula:

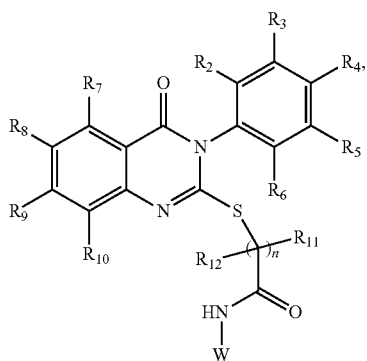

wherein W is a substituted or unsubstituted thiazoyl group and when substituted W is substituted with a $C_{1-6}$alkyl, phenyl or benzoyl group, and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, $CF_3$, and $C_{1-6}$alkyl; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof.

Embodiment 31: The compound according to Embodiment 30, wherein each of $R_2$, $R_3$, $R_6$, $R_7$, $R_8$, $R_9$ and $R_{10}$ is hydrogen and each of $R_4$ and $R_5$ is chloro.

Embodiment 32: The compound according to Embodiment 30 being selected from the group consisting of 2-[3-(3,4-dichlorophenyl)-4-oxo(3-hydroquinazolin-2-ylthio)]-N-(4-phenyl(1,3-thiazol-2-yl))acetamide; N-benzothiazol-5-yl-2-[3-(3,4-dichlorophenyl)-4-oxo(3-hydroquinazolin-2-ylthio)]acetamide; and 2-[3-(3,4-dichlorophenyl)-4-oxo(3-hydroquinazolin-2-ylthio)]-N-(4-methyl(1,3-thiazol-2-yl))acetamide; pharmaceutically acceptable salts thereof and solvates thereof.

Embodiment 33: A process for treating or preventing a viral infection in a subject, wherein said viral infection is from a flavivirus selected from the group consisting of Hepatitis C Virus (genotypes 1-7) and Japanese Encephalitis Virus, which comprises administering to said subject a therapeutically effective amount of at least one compound according to any one of Embodiments 30-32, pharmaceutically acceptable salt thereof; solvate thereof or deuterated form thereof.

Embodiment 34: A process for treating or preventing a viral infection in a subject, wherein said viral infection is from Hepatitis C Virus, which comprises administering to said subject a therapeutically effective amount of at least one compound according to any one of Embodiments 30-32, pharmaceutically acceptable salt thereof or solvate thereof.

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) typically contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

To the extent a term used in a claim is not defined above, it should be given its broadest definition persons skilled in the art have given that term as reflected in at least one printed publication or issued patent. All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

What is claimed is:

1. A process for treating or preventing a viral infection in a subject from Hepatitis C Virus, by administering to the subject a therapeutically effective amount of at least one compound selected from the group consisting of 2-[3-(3,4-dichlorophenyl)-4-oxo(3-hydroquinazolin-2-ylthio)]-N-(4-phenyl(1,3-thiazol-2-yl))acetamide; N-benzothiazol-5-yl-2-[3-(3,4-dichlorophenyl)-4-oxo(3-hydroquinazolin-2-ylthio)]acetamide; 2-[3-(3,4-dichlorophenyl)-4-oxo(3-hydroquinazolin-2-ylthio)]-N-(4-methyl(1,3-thiazol-2-yl))acetamide; N-(2,3-dihydro-1H-inden-5-yl)-2-(4-oxo-3-phenyl-3,4-dihydroquinazolin-2-yl)thio)acetamide; 2-[3-(3-chloro-4-fluorophenyl)-4-oxo(3-hydroquinazolin-2-ylthio)]-N-indan-5-ylacetamide; 2-[3-(3,4-dichlorophenyl)-4-oxo(3-hydroquinazolin-2-ylthio)]-N-indan-5-ylacetamide; 2-(5-fluoro-4-oxo-3-phenyl(3-hydroquinazolin-2-ylthio))-N-indan-5-ylacetamide; N-indan-5-yl-2-(8-methyl-4-oxo-3-phenyl(3-hydroquinazolin-2-ylthio))acetamide; N-indan-5-yl-2-(8-methoxy-4-oxo-3-phenyl(3-hydroquinazolin-2-ylthio))acetamide; 2-[3-(3,4-dichlorophenyl)-4-oxo(3-hydroquinazolin-2-ylthio)]-N-indan-4-ylacetamide; N-(2H-benzo[d]1,3-dioxolen-5-yl)-2-[3-(3,4-dichlorophenyl)-4-oxo(3-hydroquinazolin-2-ylthio)]acetamide; 3-[3-(3-chloro-4-fluorophenyl)-4-oxo(3-hydroquinazolin-2-ylthio)]-N-indan-5-ylpropanamide; 2-[3-(3-chloro-4-fluorophenyl)-4-oxo(3-hydroquinazolin-2-ylthio)]-N-indan-4-ylacetamide; N-(2H-benzo[3,4-d]1,3-dioxolan-5-yl)-2-[3-(3-chloro-4-fluorophenyl)-4-oxo(3-hydroquinazolin-2-ylthio)]acetamide; 2-[3-(3,4-difluorophenyl)-4-oxo(3-hydroquinazolin-2-ylthio)]-N-indan-4-ylacetamide; 2-[3-(3,4-difluorophenyl)-4-oxo(3-hydroquinazolin-2-ylthio)]-N-indan-5-ylacetamide; 2-(5-fluoro-4-oxo-3-phenyl(3-hydroquinazolin-2-ylthio))-N-(1,2,3,4-tetrahydronaphthyl)acetamide; 2-[3-(4-chloro-3-fluorophenyl)-5-fluoro-4-oxo(3-hydroquinazolin-2-ylthio)]-N-indan-5-ylacetamide; 2-[5-fluoro-4-oxo-3-(3,4,5-trifluorophenyl)(3-hydroquinazolin-2-ylthio)]-N-indan-5-ylacetamide; and 2-[3-(3,4-dichlorophenyl)-5-fluoro-4-oxo(3-hydroquinazolin-2-ylthio)]-N-indan-5-ylacetamide; pharmaceutically acceptable salts thereof; solvates thereof and deuterated forms thereof.

2. A process for treating or preventing a viral infection in a subject from Japanese Encephalitis Virus by administering to the subject a therapeutically effective amount of at least one compound selected from the group consisting of 2-(5-fluoro-4-oxo-3-phenyl(3-hydroquinazolin-2-ylthio))-N-indan-5-ylacetamide; 2-[3-(3,4-dichlorophenyl)-4-oxo(3-hydroquinazolin-2-ylthio)]-N-indan-4-ylacetamide; 2-[3-(2,6-dichlorophenyl)-4-oxo(3-hydroquinazolin-2-ylthio)]-N-indan-5-ylacetamide; and 2-(8-fluoro-4-oxo-3-phenyl(3-hydroquinazolin-2-ylthio))-N-indan-5-ylacetamide; pharmaceutically acceptable salts thereof solvates thereof and deuterated forms thereof.

3. A process for treating or preventing a viral infection in a subject from West Nile Virus by administering to the subject a therapeutically effective amount of at least one compound selected from the group consisting of: 2-[3-(2-fluorophenyl)-4-oxo(3-hydroquinazolin-2-ylthio)]-N-indan-5-ylacetamide; 2-[3-(3-chloro-4-fluorophenyl)-4-oxo(3-hydroquinazolin-2-ylthio)]-N-indan-5-ylacetamide; 2-[3-(3,4-dichlorophenyl)-4-oxo(3-hydroquinazolin-2-ylthio)]-N-indan-5-ylacetamide; 2-[3-(3,5-dichlorophenyl)-4-oxo(3-hydroquinazolin-2-ylthio)]-N-indan-5-ylacetamide; 2-[3-(3,4-difluorophenyl)-4-oxo(3-hydroquinazolin-2-ylthio)]-N-indan-5-ylacetamide, 2-[3-(3,4-dichlorophenyl)-5-fluoro-4-oxo(3-hydroquinazolin-2-ylthio)]-N-indan-5-ylacetamide; N-indan-5-yl-2-(4-oxo-3-phenyl(3-hydroquinazolin-2-ylthio))acetamide; 2-[3-(4-chloro-3-methylphenyl)-4-oxo(3-hydroquinazolin-2-ylthio)]-N-indan-5-ylacetamide; 2-[3-(4-fluoro-3-methylphenyl)-4-oxo(3-hydroquinazolin-2-ylthio)]-N-indan-5-ylacetamide; N-indan-5-yl-2-[4-oxo-3-(3,4,5trifluorophenyl)(3-hydroquinazolin-2-ylthio)]acetamide; 2-[3-(3-bromo-4-methylphenyl)-4-oxo(3-hydroquinazolin-2-ylthio)]-N-indan-5-ylacetamide; 2-[3-(3,4-dichlorophenyl)-8-fluoro-4-oxo(3-hydroquinazolin-2-ylthio)]-N-indan-5-ylacetamide; 2-[3-(3,5-difluorophenyl)-4-oxo(3-hydroquinazolin-2-ylthio)]-N-indan-5-ylacetamide; 2-[3-(3,5-dichlorophenyl)-8-fluoro-4-oxo(3-hydroquinazolin-2-ylthio)]-N-indan-5-ylacetamide; 2-[3-(2,6-dichlorophenyl)-4-oxo(3-hydroquinazolin-2-ylthio)]-N-indan-5-ylacetamide; 2-[3-(3-bromo-4-chlorophenyl)-4-oxo(3-hydroquinazolin-2-ylthio)]-N-indan-5-ylacetamide; 2-(8-fluoro-4-oxo-3-phenyl(3-hydroquinazolin-2-ylthio))-N-indan-5-ylacetamide; and 2-[3-(4,5-difluoro(2-pyridyl))-4-oxo(3-hydroquinazolin-2-ylthio)]-N-indan-5-ylacetamide; pharmaceutically acceptable salts thereof; solvates thereof and deuterated forms thereof.

4. A process for treating or preventing a viral infection in a subject, wherein said viral infection is from a flavivirus selected from the group consisting of Hepatitis C Virus (genotypes 1-7) and Japanese Encephalitis Virus, which comprises administering to said subject a therapeutically effective amount of a compound represented by formula:

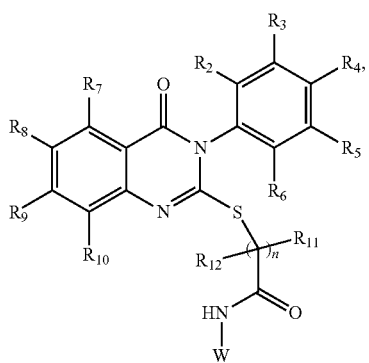

wherein W is a substituted or unsubstituted thiazoyl group and when substituted W is substituted with a $C_{1-6}$alkyl, phenyl or benzoyl group, and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, $CF_3$, and $C_{1-6}$alkyl; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof.

5. The process for treating or preventing a viral infection in a subject according to claim 4, wherein each of $R_2$, $R_3$, $R_6$, $R_7$, $R_8$, $R_9$ and $R_{10}$ is hydrogen and each of $R_4$ and $R_5$ is chloro.

6. The process for treating or preventing a viral infection in a subject according to claim 4, wherein the compound is selected from the group consisting of 2-[3-(3,4-dichlorophenyl)-4-oxo(3-hydroquinazolin-2-ylthio)]-N-(4-phenyl(1,3-thiazol-2-yl))acetamide; N-benzothiazol-5-yl-2-[3-(3,4-dichlorophenyl)-4-oxo(3-hydroquinazolin-2-ylthio)]acetamide; and 2-[3-(3,4-dichlorophenyl)-4-oxo(3-hydroquinazolin-2-ylthio)]-N-(4-methyl(1,3-thiazol-2-yl))acetamide; pharmaceutically acceptable salts thereof; solvates thereof and deuterated forms thereof.

7. A process for treating or preventing a viral infection in a subject according to claim 4, wherein said viral infection is from Hepatitis C Virus.

8. A process for treating or preventing a viral infection in a subject, wherein said viral infection is from a flavivirus selected from the group consisting of Hepatitis C Virus (genotypes 1-7) and Japanese Encephalitis Virus, which comprises administering to said subject a therapeutically effective amount of at least one compound represented by the formula:

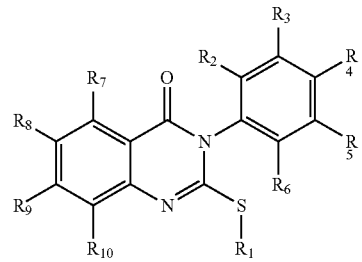

wherein $R_1$ is represented by the formula:

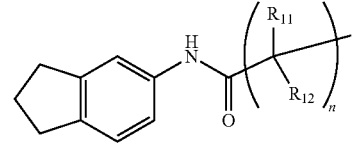

and each $R_2$, $R_3$, $R_4$, $R_5$, $R_6$, $R_7$, $R_8$, $R_9$ and $R_{10}$ is independently selected from the group consisting of H, halogen, hydroxy, amino, nitro, cyano, formyl, $CF_3$, $S(C_{1-4}$alkyl), $S(O)C_{1-4}$alkyl, $S(O)_2C_{1-4}$alkyl, $C_{1-4}$alkylcarbonyl, $C_{1-6}$alkyl, hydroxy $C_{1-6}$alkyl, $C_{1-6}$alkoxy, halo$C_{1-6}$alkoxy, hydroxy $C_{1-6}$ alkoxy, $C_{2-6}$alkenyl, $C_{2-6}$alkynyl, $C_{1-6}$alkylamino, di($C_{1-6}$alkyl)amino; $R_{11}$ and $R_{12}$ are independently selected from the group consisting of H, halogen, hydroxyl, $C_{1-6}$alkoxy, amino, nitro, cyano, $CF_3$ and $C_{1-4}$alkyl; n is zero, one, two, three or four, five or six; pharmaceutically acceptable salts thereof; solvates thereof and deuterated forms thereof.

9. The process of claim 4, wherein said alkyl and said alkoxy contain 1 to 4 carbon atoms.

10. The process of claim 4, wherein R substituents of said compound are selected from the group consisting of a) each of $R_2$, $R_4$, $R_5$, $R_6$, $R_7$, $R_8$, $R_9$ and $R_{10}$ is H and $R_3$ is F; b) each of $R_2$, $R_5$, $R_6$, $R_7$, $R_8$, $R_9$ and $R_{10}$ is H, $R_3$ is Cl and $R_4$ is F; c) each of $R_2$, $R_5$, $R_6$, $R_7$, $R_8$, $R_9$ and $R_{10}$ is H and $R_3$ and $R_4$ are each Cl; d) each of $R_2$, $R_3$, $R_5$, $R_6$, $R_7$, $R_8$, $R_9$ and $R_{10}$ is H and $R_4$ is F; e) each of $R_2$, $R_3$, $R_4$, $R_5$, $R_6$, $R_7$, $R_9$ and $R_{10}$ is H and $R_8$ is F; f) each of $R_2$, $R_3$, $R_4$, $R_5$, $R_6$, $R_7$, $R_9$ and $R_{10}$ is H and $R_8$ is $CH_3$; g) each of $R_2$, $R_3$, $R_4$, $R_5$, $R_6$, $R_8$, $R_9$ and $R_{10}$ is H and $R_7$ is F; h) each of $R_2$, $R_3$, $R_4$, $R_5$, $R_6$, $R_8$, $R_9$ and $R_{10}$ is H and $R_7$ is I; i) each of $R_2$, $R_3$, $R_4$, $R_5$, $R_6$, $R_7$, $R_8$ and $R_9$ is H and $R_{10}$ is $CH_3$; j) each of $R_2$, $R_3$, $R_4$, $R_5$, $R_6$, $R_7$, $R_8$ and $R_9$ is H and $R_{10}$ is $OCH_3$; kj) each of $R_2$, $R_4$, $R_6$, $R_7$, $R_8$, $R_9$ and $R_{10}$ is H and each of $R_3$ and $R_5$ is Cl; l) each of $R_2$, $R_6$, $R_7$, $R_8$, $R_9$ and $R_{10}$ is H and each of $R_3$, $R_4$ and $R_5$ is F; m) each of $R_2$, $R_3$, $R_4$, $R_5$, $R_6$, $R_8$, $R_9$ and $R_{10}$ is H and $R_7$ is F; n) each of $R_2$, $R_5$, $R_6$, $R_8$, $R_9$ and $R_{10}$ is H and each of $R_3$ and $R_7$ is F and $R_4$ is Cl; o) each of $R_2$, $R_3$, $R_6$, $R_8$, $R_9$ and $R_{10}$ is H and each of $R_4$, $R_5$ and $R_7$ is F; p) each of $R_2$, $R_5$, $R_6$, $R_8$, $R_9$ and $R_{10}$ is H and each of $R_3$, $R_4$ and $R_7$ is F; q) each of each $R_2$, $R_6$, $R_8$, $R_9$ and $R_{10}$ is H and each of $R_3$, $R_4$, $R_5$ and $R_7$ is F; r) each $R_2$, $R_3$, $R_6$, $R_8$, $R_9$ and $R_{10}$ is H, each of $R_4$ and $R_5$ is Cl and $R_7$ is F; s) each $R_2$, $R_5$, $R_6$, $R_8$, $R_9$ and $R_{10}$ is H, each of $R_3$ and $R_4$ is Cl and $R_7$ is F; t) each $R_2$, $R_3$, $R_6$, $R_8$, $R_9$ and $R_{10}$ is H, $R_5$ is Br and each of $R_4$ and $R_7$ is F; and u) each $R_2$, $R_4$, $R_6$, $R_8$, $R_9$ and $R_{10}$ is H, $R_3$ is Br and each of $R_4$ and $R_7$ is F.

* * * * *

UNITED STATES PATENT AND TRADEMARK OFFICE
CERTIFICATE OF CORRECTION

| | |
|---|---|
| PATENT NO. | : 9,598,402 B2 |
| APPLICATION NO. | : 14/238346 |
| DATED | : March 21, 2017 |
| INVENTOR(S) | : Marintha L. Heil et al. |

It is certified that error appears in the above-identified patent and that said Letters Patent is hereby corrected as shown below:

In the Specification

In Column 1, Lines 17 through 20, please replace:
"This invention was partially supported by grants No. 1 R03 MN084847-01 and 5U54HG0053034 from the National Institutes of Health and the US Government has certain rights in the invention."
With:
"This invention was made with government support under MN084847, and HG005034 awarded by the National Institutes of Health. The government has certain rights in the invention."

Signed and Sealed this
Seventeenth Day of September, 2024

*Katherine Kelly Vidal*

Katherine Kelly Vidal
*Director of the United States Patent and Trademark Office*